US008158341B2

(12) United States Patent
Peddada et al.

(10) Patent No.: US 8,158,341 B2
(45) Date of Patent: *Apr. 17, 2012

(54) EFFICIENT ALGORITHM FOR PCR TESTING OF BLOOD SAMPLES

(75) Inventors: Lorraine B. Peddada, Arcadia, CA (US); Charles M. Heldebrant, Arcadia, CA (US); Andrew J. Conrad, Malibu, CA (US); Peter Schmid, Los Angeles, CA (US)

(73) Assignee: Baxter International Inc., Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/374,484

(22) Filed: Mar. 9, 2006

(65) Prior Publication Data
US 2006/0160073 A1 Jul. 20, 2006

Related U.S. Application Data

(60) Division of application No. 10/442,780, filed on May 20, 2003, now abandoned, which is a division of application No. 09/549,477, filed on Apr. 14, 2000, now Pat. No. 6,566,052, which is a division of application No. 09/081,926, filed on May 20, 1998, now Pat. No. 6,063,563, which is a division of application No. 08/778,610, filed on Jan. 6, 1997, now Pat. No. 5,780,222, which is a continuation-in-part of application No. 08/683,784, filed on Jul. 16, 1996, now Pat. No. 5,834,660, which is a division of application No. 08/419,620, filed on Apr. 10, 1995, now Pat. No. 5,591,573.

(51) Int. Cl.
*C12Q 1/70* (2006.01)
*C12Q 1/68* (2006.01)

(52) U.S. Cl. ............................ 435/5; 435/91.2; 536/25.3

(58) Field of Classification Search ........................ None
See application file for complete search history.

(56) References Cited

U.S. PATENT DOCUMENTS

| 2,870,583 | A | 1/1959 | Flax |
| 2,940,230 | A | 6/1960 | Flax |
| 3,855,868 | A | 12/1974 | Sudvaniemi |
| 4,176,451 | A | 12/1979 | McMorrow |
| 4,363,205 | A | 12/1982 | Hollander, Jr. |
| 4,478,095 | A | 10/1984 | Bradley et al. |
| 4,527,383 | A | 7/1985 | Bingham |
| 4,678,894 | A | 7/1987 | Shafer |
| 4,683,202 | A | 7/1987 | Mullis |
| 4,713,974 | A | 12/1987 | Stone |
| 4,820,297 | A | 4/1989 | Kaufman et al. |
| 4,833,071 | A | 5/1989 | Wang et al. |
| 4,846,005 | A | 7/1989 | Bacehowski et al. |
| 4,900,321 | A | 2/1990 | Kaufman et al. |
| 5,176,995 | A | 1/1993 | Sninsky et al. |
| 5,364,526 | A | 11/1994 | Matkovich et al. |
| 5,394,907 | A | 3/1995 | Hjertman et al. |
| 5,423,792 | A | 6/1995 | Oxley |
| 5,464,740 | A | 11/1995 | Chasalow |
| 5,475,610 | A | 12/1995 | Atwood et al. |
| 5,591,573 | A | 1/1997 | Whalen et al. |
| 5,780,222 | A | 7/1998 | Peddada et al. |
| 5,834,660 | A | 11/1998 | Whalen et al. |
| 6,063,563 | A | 5/2000 | Peddada et al. |
| 6,566,052 | B1 | 5/2003 | Peddada et al. |

FOREIGN PATENT DOCUMENTS

| EP | 0248690 | 12/1987 |
| EP | 0248690 A1 | 12/1987 |
| WO | WO 93/16201 | 8/1993 |
| WO | WO98/16201 | 8/1993 |
| WO | WO-96/35437 | 11/1996 |
| WO | WO 96/35437 | 11/1996 |
| WO | WO 98/30723 | 7/1998 |

OTHER PUBLICATIONS

Pirrung et al. "Preparation and Screenig against Acetylcholinesterase of a Non-Peptide "Indexed" Combinatorial Library," J. Am. Chem. Soc., vol. 117, pp. 1240-1245 (1995).*
McOmish et al. Detection of Parvovirus B19 in Dontated Blood: a Model System for Screening by Polymerase Chain Reaction, J. Clinic. Microb., vol. 31, pp. 323-328 (1993).*
da Silva et al. "Prevalence of HCV-RNA-positive blood donors and correlation of ELISA and RIBA status," Ann. Hematol., vol. 66, pp. 147-151 (1993).*
Phatarfod et al., "The use of a square array scheme in blood testing," Statistics in Medicine, vol. 13, p. 2337-2343 (1994).* Barillot, et al., "Theoretical Analysis of Library Screening Using a N-dimensional Pooling Strategy," *Nucleic Acids Research*, 1991, pp. 6241-6247, vol. 19, No. 22, Oxford University Press.
Bonnema, et al., "An Improved Method of Partially Digesting Plant Megabase DNA Suitable for YAC Cloning: Application to the Construction of a 5.5 Genome Equivalent YAC Library of Tomato," *The Plant Journal*, 1996, pp. 125-133, vol. 9, No. 1.
Busch, et al., "Evaluation of Screened Blood Donations for Human Immunodeficiency Virus Type 1 Infection by Culture and DNA Amplification of Pooled Cells," *The New England Journal of Medicine*, Jul. 4, 1991, pp. 1-5, vol. 325, No. 1, The Massachusetts Medical Society.

(Continued)

*Primary Examiner* — Marjorie Moran
*Assistant Examiner* — Anna Skibinsky
(74) *Attorney, Agent, or Firm* — Kauth, Pomeroy, Peck & Bailey LLP

(57) ABSTRACT

A method is provided for identifying viral positive biological fluid donations in the fewest number of test cycles. The method comprises providing biological fluid donations and defining an n-dimensional matrix comprising a multiplicity of elements, each element being identified by a matrix notation comprising an index for each dimension of the array. Samples are taken from each fluid donation and mapped to a matrix element with each sample identified by its corresponding element's notation; n aliquots being taken from each sample and subpools formed from the aliquots with each subpool containing an aliquot from all samples mapped to elements in which one of the dimensional indices is fixed. Subpools are tested for viral indication and the dimensional index of each subpool that returns a positive viral indication is determined. The dimensional indices are combined to identify a subset of matrix elements that contain a viral positive sample.

94 Claims, 16 Drawing Sheets

OTHER PUBLICATIONS

Cardoso, et al., "Safety of Blood Products Derived from Plasma Pools: The Positive Impact of Anti-HCV Screening on the Quality of Such Products," *Vox Sanguinis*, 1996, pp. 184-186, vol. 71, Karger.

Garcia, et al., "Evaluation of a Pooling Method for Routine Anti-HCV Screening of Blood Donors to Lower the Cost Burden on Blood Banks in Countries Under Development," *Journal of Medical Virology*, Jul. 1996, pp. 218-222, vol. 49, No. 3.

Gresser, I., ed., *Interferon*, 1981, p. 102, vol. 3, Academic Press, NY.

Jones, et al., "A Set of Ninety-Seven Overlapping Yeast Artificial Chromosome Clones Spanning the Human Y Chromosome Euchromatin," *Genomics*, 1994, pp. 266-275, vol. 24.

Kim, et al., "Recombinant Fragment Assay for Gene Targeting Based on the Polymerase Chain Reaction," *Nucleic Acids Research*, 1988, pp. 8887-8903, vol. 16, No. 18.

Matsuda, et al., "Preliminary Report on an Automated Screening Test for Detection of Antibody to Human Immunodeficiency Virus Type 1 in Whole Blood," *Clinical Infectious Diseases*, 1994, pp. 327-328, vol. 19.

McOmish, et al., "Detection of Parvovirus B19 in Donated Blood: A Model System for Screening by Polymerase Chain Reaction," *Journal of Clinical Microbiology*, Feb. 1993, pp. 323-328, vol. 31, No. 2, American Society for Microbiology.

McOmish et al., "Failure to Detect Hepatitis A Virus RNA in Factor VIII Concentrates Using the Polymerase Chain Reaction," *Vox Sanguinis*, 1994, pp. 47-50, vol. 67 (suppl), Karger.

Mortimer, "Intersecting Pools and Their Potential Application in Testing Donated Blood for Viral. Genomes," *Vox Sanguinis*, 1997, pp. 93-96, vol. 73, Karger.

Nübling, et al., "GB-C Genomes in a High-Risk Group, in Plasma Pools, and in Intravenous Immunoglobulin," *The Lancet*, Jan. 6, 1996, p. 68, vol. 347.

Nübling, et al., Virus Testing of Plasma Pools and Blood Products by Nucleic Acid Amplification, *Hämostaseologie*, 1996, pp. 274-276, vol. 16.

Pirrung, et al., "Preparation and Screening Against Acetylcholinesterase of a Non-Peptide 'Indexed' Combinatorial Library," *J. Am. Chem. Soc.*, 1995, pp. 1240-1245, vol. 117.

Saldanha, "Assays for Viral Sequences and Their Value in Validation of Viral Elimination," *Virological Safety Aspects of Plasma Derivatives, Dev., Biol. Stand. Basel*. Brown, F. Ed., Karger, 1993, pp. 231-236, vol. 81.

Saldanha, et al., "A Sensitive PCR Method for Detecting HCV RNA in Plasma Pools, Blood Products, and Single Donations," *Journal of Medicine Virology*, 1994, pp. 72-76, vol. 43.

Saldanha, et al., "Collaborative Study to Assess the Suitability of an HCV RNA Reference Sample for Detection of an HCB RNA in Plasma Pools by PCR," *Vox Sanguinis*, 1996, pp. 148-151, vol. 70.

Saldanha, et al., "Detection of Human Parvovirus B19 DNA in Plasma Pools and Blood Products Derived From These Pools: Implications for Efficiency and Consistency of Removal of B19 DNA During Manufacture," *British Journal of Haematology*, 1996, pp. 714-719, vol. 93.

Saldanha, et al., "Incidence of Hepatitis C Virus RNA in Anti-HCV-Negative Plasma Pools and Blood Products," *Vox Sanguinis*, 1996, pp. 232-234, vol. 70.

Schmidt, et al., "Typing of Echo Virus Isolates by Immune Serum Pools the "Intersecting Serum Scheme,"" *The Journal of Immunology*, Nov. 1961, cover page, pp. 623-626, vol. 87, No. 5, The Williams & Wilkins Company, Baltimore.

Smith, et al., "Synthesis and Biological Evaluation of a Library Containing Potentially 1600 Amides/Esters. A Strategy for Rapid Compound Generation and Screening," *Bioorg. Med. Chem. Lett.*, 1994, pp. 2821-2824, vol. 4, No. 24.

Umehara, et al., "An Ordered Yeast Artificial Chromosome Library Covering Over Half of Rice Chromosome 6," *Genome Research*, 1996, pp. 935-942, Cold Spring Harbor Laboratory Press.

Weissmann, "The Cloning of Interferon and Other Mistakes," *Interferon*, 1981, cover page, pp. 101-133, Gressler, Ed., Academy Press.

Zakrzewska, et al., "Human Parvovirus B19 in Clotting Factor Concentrates: B19 DNA Detection by the Nested Polymerase Chain Reaction," *British Journal of Hematology*, 1992, pp. 407-412, vol. 81.

Zeijlemaker, et al.,"EPFA-NIBSC Workshop on Nucleic Acid Amplification Assays and Plasma Products," *Biologicals*, Nov. 23, 1994, pp. 317-326, vol. 23, Helsinki, Finland.

Office Action dated Nov. 29, 2007, issued in U.S. Appl. No. 11/318,128.

"Complaint for Patent Infringement" for Civil Action No. 5:08-CV-00238-FL, dated May 21, 2008, 114 pages.

"Civil Cover Sheet" for Civil Action No. 5:08-CV-00238-FL, dated May 21, 2008, 2 page.

"Disclosure of Corporate Affiliations and Other Entities with a Direct Financial Interest" in Litigation for Case No. 08-CV-238, dated May 21, 2008, 2 pages.

"Summons in a Civil Action" for Case No. 08-CV-238, 1 page.

"Withdrawal of Motion" for Case 5:08-CV-00238-FL, Document 15, filed Jun. 30, 2008, 3 pages.

"Defendant's Motion to Dismiss Complaint for Patent Infringement for Lack of Subject Matter Jurisdiction Due to Plaintiff's Lack of Standing" for Case 5:08-CV-00238-FL, Document 19; filed Aug. 14, 2008, 5 pages.

"Declaration of Jacob S. Wharton" for Civil Action No. 5:08-CV-00238-FL, dated Aug. 14, 2008, 11 pages.

"Memorandum in Support of Defendant's Motion to Dismiss Complaint for Patent Infringement for Lack of Subject Matter Jurisdiction Due to Plaintiffs' Lack of Standing" for Civil Action No. 5:08-CV-00238-FL, dated Aug. 14, 2008, 7 pages.

"Initial Order Regarding Planning and Scheduling" for Case 5:08-CV-00238-FL, filed Aug. 28, 2008, 7 pages.

"Order" for Case 5:08-CV-00238-FL, Document 16, filed Jul. 1, 2008, 1 page.

"Defendant's Motion for Extension of Time to Respond to Plaintiffs' Complaint (Fed.R.Civ. P. 6(b))" for Case 5:08-CV-00238-FL, Document 7, filed Jun. 27, 2008, 4 pages.

"Stipulation Extending Defendant's Time to Serve Its Answer, Motion or Other Response" for Case 5:08-CV-00238-FL, Document 14, filed Jun. 30, 2008, 4 pages.

"Complaint for Patent Infringement" for Civil Action No. 5:08-CV-464-H, dated Sep. 15, 2008, 119 pages.

"Civil Cover Sheet" for Civil Action No. 5:08-CV-464-H, dated Sep. 15, 2008, 1 page.

"Summon in a Civil Action" for Case No. 5:08-CV-464-H, dated Sep. 16, 2008, 2 pages.

"Affidavit of Process" for Case No. 08 cv 464-HS, dated Sep. 16, 2008, 1 page.

"Notice of Voluntary Dismissal" for Case 5:08-cv-00238-FL, Document 26, Filed Sep. 15, 2008, 3 pages.

"Consent Motion to Extend Time for Defendant to Answer or Otherwise Plead" for Civil Action No. 5:08-CV-464-H, dated Oct. 6, 2008, 6 pages.

"Order" for No. 5:08-CV-464-H, dated Oct. 9, 2008, 1 page.

"Notice of Filing of Correct Exhibit" for Case No. 5:08-CV-464-H, dated Oct. 21, 2008, 10 pages.

"Notice of Assignment of Reexamination Request" for Reexam Control No. 90/009,326, filed Nov. 7, 2008, 1 page.

"Notice of Reexamination Request Filing Date" for Reexam Control No. 90/009,326, filed Nov. 7, 2008, 1 page.

"Request for Ex Parte Reexamination Transmittal Form" for Patent No. 5,780,222, issued Jul. 14, 2008, 16 pages.

"Information Disclosure Statement by Requester" Application No. 90/009,326, filing date Nov. 7, 2008, 2 pages.

"Notice of Assignment of Reexamination Request" for Reexam Control No. 90/009,324, filed Nov. 7, 2008, 1 page.

"Notice of Reexamination Request Filing Date" for Reexam Control No. 90/009,324, filed Nov. 7, 2008, 1 page.

"Request for Ex Parte Reexamination Transmittal Form" for Patent No. 6,063,563, issued May 16, 2000, 19 pages.

"Information Disclosure Statement by Requester" for Application No. 90/009,324, filing date Nov. 7, 2000, 2 pages.

"Notice of Reexamination Request Filing Date" for Reexam Control No. 90/009,325, filed Nov. 7, 2008, 1 page.

"Notice of Assignment of Reexamination Request" for Reexam Control No. 90/009,325, filed Nov. 7, 2008, 1 page.

"Request for Ex Parte Reexamination Transmittal Form" for Patent No. 6,566,052, issued May 20, 2003, 17 pages.

"Information Disclosure Statement by Requester" for Application No. 90/009,325, filing date Nov. 7, 2008, 2 pages.
Kenny et al., "Analysis of Serum Pooling Schemes for Identification of Large Numbers of Viruses", American Journal of Epidemiology, 1970, vol. 91, No. 4, pp. 439-445.
Office Action dated Nov. 29, 2007, issued in U.S. Appl. No. 11/318,128, 12 pgs.
Heredia et al., "Development of a multiplex PCR assay for the simultaneous detection and discrimination of HIV-1, HIV-2, HTLV-I and HTLV-II", Clinical and Diagnostic Virology, 1996, Vol. 7, pp. 85-92.
Saldanha et al., "A Sensitive PCR Method for Detecting HCV RNA in Plasma Pools, Blood Products, and Single Donations", Journal of Medical Virology, 1994, vol. 43, pp. 72-76.
Garcia et al., "Evaluation of a Pooling Method for Routine Anti-HCV Screening of Blood Donors to Lower the Cost Burden on Blood Banks in Countries Under Development", Journal of Medical Virology, 1996, vol. 49, pp. 218-222.
Ottmann et al., "The polymerase chain reaction for the detection of HIV-1 genomic RNA in plasma from infected individuals", Journal of Virological Methods, 1991, vol. 31, pp. 273-283.
Aslanzadeh et al., "Evaluation of PCT and Nested PCT for Laboratory Diagnosis of Hepatitis C Virus Infection", Molecular and Cellular Probes, 1996, vol. 10, pp. 173-178.
Bonnema et al., "An Improved Method of Partially Digesting Plant Megabase DNA Suitable for YAC Cloning: Application to the Construction of a 5.5 Genome Equivalent YAC Library of Tomato," The Plant Journal, 1996, vol. 9, No. 1, pp. 125-133.
Busch et al., "Evaluation of Screened Blood Donations for Human Immunodeficiency Virus Type 1 Infection by Culture and DNA Amplification of Pooled Cells," The New England Journal of Medicine, Jul. 4, 1991, vol. 325, No. 1, The Massachusetts Medical Society, pp. 1-5.
Cardoso et al., "Safety of Blood Products Derived from Plasma Pools: The Positive Impact of Anti-HCV Screening on the Quality of Such Products," Vox Sanguinis, 1996, vol. 71, Karger, pp. 184-186.
Choo et al., "Isolation of cDNA clone derived from a blood-borne non-A, non-B viral hepatitis genome", Science 1989; vol. 244, pp. 359-362.
Civil Cover Sheet for Civil Action No. 5:08-CV-00238-FL, dated May 21, 2008, 2 pages.
Civil Cover Sheet for Civil Action No. 5:08-CV-464-H, dated Sep. 15, 2008, 1 pg.
Complaint for Patent Infringement for Civil Action No. 5:08-CV-00238-FL, dated May 21, 2008, 114 pages.
Complaint for Patent Infringement for Civil Action No. 5:08-CV-464-H, dated Sep. 15, 2008, 119 pages.
Da Silva et al., "Prevalence of HCV-RNA-Positive Blood Donors and Correlation of ELISA and RIBA Status", Ann. Hematol., 1993, vol. 66., pp. 147-151.
Dorfman, "The Detection of Defective Members of Large Populations," Annals of Mathematical Statistics, 1943, vol. 40, pp. 436-440.
Dorner et al., "A Quality-Assured Gene Amplification Assay System (PCR) for Use on an Industrial Scale—a Proposal for Validation", Clin. La., 1996, vol. 42, pp. 89-882.
Emmanuel, "Pooling of Sera for Human Immunodeficiency Virus (HIV) Testing: An Economical Method for Use in Developing Countries", J. Clin. Pathol., 1988, vol. 41, pp. 582-585.
Farma et al., "Single Step" PCT with a Sensitivity Similar to Nested PCT for the Detection of Hepatitis C Virus RNA, Clinical and Experimental Rheumatology, 1995, vol. 13, pp. S59-S61.
Finney, The Estimation of the Mean of a Normal Tolerance Distribution. Sankhya: The Indian Journal of Statistics, 1950, vol. 10, pp. 341-361.
Finucan, "The Blood Testing Problem", Applied Statistics, 1965, vol. 13, pp. 43-50, 210.
Food and Drug Administration, Center for Biologics Evaluation and Research, Fifty-Fourth Meeting of the Blood Products Advisory Committee, Mar. 1997, 303 pgs.
Garcia et al., "Evaluation of a Pooling Method for Routine Anti-HCV Screening of Blood Donors to Lower the Cost Burden on Blood Banks in Countries Under Development," Journal of Medical Virology, Jul. 1996, vol. 49, No. 3, pp. 218-222.

Green et al., "Systematic Screening of Yeast Artificial-Chromosome Libraries by Use of the Polymerase Chain Reaction", Proc. Natl. Acad. Sci. USA, Feb. 1990, vol. 87, pp. 1213-1217.
Hanley et al., If nothing goes wrong, is everything all right: interpreting zero numerators, J Am Med Assoc 1983; vol. 249, pp. 1943-1745.
Hart et al., "A Comparison of Polymerase Chain Reaction and an Infectivity Assay for Human Immunodeficiency Virus Type I Titration During Virus Inactivation of Blood Components", Transfusion, 1993, vol. 33, No. 10, pp. 838-841.
Holodniy et al., "Inhibition of Human Immunodeficiency Virus Gene Amplification by Heparin", Journal of Clinical Microbiology, Apr. 1991, vol. 29, No. 4, pp. 676-679.
Imai et al., "Screening of YAC Library", Tanpakushitsu, Kakusan, Koso (Protein, Nucleic Acid and Enzyme), 1993, vol. 38, No. 3, pp. 591-599 (Japanese).
Imai et al., "Screening of YAC Library", Tanpakushitsu, Kakusan, Koso (Protein, Nucleic Acid and Enzyme), 1993, vol. 38, No. 3, pp. 591-599 (English translation).
Information Disclosure Statement by Requester for Application No. 90/009,326, filing date Nov. 7, 2008, 2 pages.
Information Disclosure Statement by Requester for Application No. 90/009,324, filing date Nov. 7, 2008, 2 pages.
Information Disclosure Statement by Requester for Application No. 90/009,325, filing date Nov. 7, 2008, 2 pages.
IQ-PCR: DNA—Technologie im Dienste der Virussicherheit Biologischer Anznemittle, Immuno, Jan. 1996, 16 pgs.
Jones et al., "A Set of Ninety-Seven Overlapping Yeast Artificial Chromosome Clones Spanning the Human Y Chromosome Euchromatin," Genomics, 1994, vol. 24, pp. 266-275.
Karber, Method of Analysis:, ORDP 20-111, Chapters 10-3-10-7.
Karber, "On the Collective Treatment of Pharmacological Test Series", The Pharmacoogical Institute of the University of Leipzig, Aug. 1931, 3 pgs. (English).
Karber, Beitrag zur Kollektiven Behandlung Pharmakologischer Reihenversuche (German).
Kim et al., "Recombinant Fragment Assay for Gene Targeting Based on the Polymerase Chain Reaction," Nucleic Acids Research, 1988, vol. 16, No. 18, pp. 8887-8903.
Kruskal et al., Use of Ranks in One-Criteron Variance Analysis. Journal of the American Statiscal Association, Dec. 1952, vol. 47, No. 260, p. 583619.
Kuhnl et al., "Reduction of virus load in blood donations by screening methods", Morgenthaler J.J., ed. Virus Inactivation in Plasma Products. Basel: Karger; 1989:9-22.
Kuo et al., "An assay for circulating antibodies to a major etiologic virus of human non-A, non-B hepatitis", Science 1989; vol. 244, pp. 362-364.
Kwok et al., "Avoiding False Positives with PCT", Nature, May 18, 1989, vol. 339, pp. 237-238.
Lackritz et al., Estimated risk of transmission of the Human Immunodeficiency Virus by screened blood in the United States:, N. Engl J Med 1995; vol. 333, pp. 1721-1725.
Lin et al., "Polymerase Chain Reaction Assay for Hepatitis C Virus RNA Using a Single Tube for Reverse Transcription and Serial Rounds of Amplification with Nested Primer Pairs", Journal of Medical Virology, 1992, vol. 38, pp. 220-225.
Mullis et al., "Specific Synthesis of DNA in Vitro via a Polymerase-Catalyzed Chain Reaction", Methods in Enzymology, 1987, pp. 335-350.
Nakagiri et al., "Analysis of discordant test results among five second generation assays for anti-hepatitis C virus antibodies also tested by polymerase chain reaction-RNA assay and other laboratory and clinical tests for hepatitis", J Clin Microbiol 1993; vol. 31, pp. 2974-2980.
Nalpas et al., "Hepatitis C viremia and anti-HCV antibodies in alcoholics", J. Hepatol 1992; vol. 14, pp. 381-384.
Natrella, "Experimental Statistics", National Bureau of Standards Handbook 91, Aug. 1, 1963, Chapter 3-22-3-30.
Nishiguchi et al., Detection of hepatitis C virus antibody in the absence of viral RNA in patients with autoimmune hepatitis:, Ann Intern Med 1992; 116:21-25.
Notice of Voluntary Dismissal for Case 5:08-cv-00238-FL, Document 26, Filed Sep. 15, 2008, 3 pages.

Office Action for U.S. Appl. No. 10/442,780 dated Jan. 25, 2007, 14 pgs.
Office Action for U.S. Appl. No. 10/442,780 dated Jun. 28, 2007, 13 pgs.
Office Action for U.S. Appl. No. 10/442,780 dated May 8, 2006, 9 pgs.
Office Action for U.S. Appl. No. 10/442,780 dated Dec. 29, 2008, 15 pgs.
Office Action for U.S. Appl. No. 10/442,780 dated Apr. 2, 2008, 16 pgs.
Office Action for U.S. Appl. No. 11/318,128 dated Oct. 3, 2008, 9 pgs.
Office Action for U.S. Appl. No. 11/318,128 dated Jan. 25, 2007, 10 pgs.
Office Action for U.S. Appl. No. 11/318,128 dated Nov. 29, 2007, 12 pgs.
Ou et al., "DNA Amplification for Direct Detection of HIV-1 in DNA of Peripheral Blood Mononuclear Cells", Science, Jan. 15, 1988, vol. 239, pp. 295-297.
Payan et al., "Single-Step Reverse Transcription-Polymerase Chain Reaction for Hepatitis C Virus RNA with DNA Enzyme Immunoassay Hybridization", Journal of Virological Methods, 1995, vol. 53, pp. 167-175.
Petersen et al., "Duration of time from onset of human immunodeficiency virus type 1 infectiousness to development of antibody", Transfusion 1994; vol. 34, pp. 283-289.
Rogers et al., "Report of EPFA/NIBSC Workshop 'Nucleic Acid Amplification Tests (NAT) for the Detection of Blood-Borne Viruses' Held on Oct. 31, 1996 in Amsterdam, The Netherlands", Vox Sang, 1997, vol. 72, pp. 199-206.
Sankary et al., "Rare detection of hepatitis B and hepatitis C virus genomes by polymerase chain reaction in seronegative donors with elevated alanini aminotransferase", Transfusion, 1994, vol. 19, No. 22, pp. 656-660.
Scadden et al., "Quantitation of Plasma Human Immunodeficiency Virus Type 1 RNA by Competitive Polymerase Chain Reaction", JID, 1992, vol. 165, pp. 1119-1123.
Scheiblauer et al., "Prevalence of hepatitis C virus in plasma pools and the effectiveness of cold ethanol fractionation", Clin Therapeut 1996; vol. 18, pp. 59-70.
Schottstedt et al., "Routine PCR Screening for HBV, HCV and HIV-1 Genome in a Large-Scale Blood Transfusion Service—Experiences and Initial Results", Transfusionsmedizin, 1996/97, Beitr Infusionsther Transfusionsmed. Basel, Karger, 1997, vol. 34, pp. 21-25 (English translation).
Schottstedt et al., "Routine PCR Screening for HBV, HCV and HIV-1 Genome in a Large-Scale Blood Transfusion Service—Experiences and Initial Results", Transfusionsmedizin, 1996/97, Beitr Infusionsther Transfusionsmed. Basel, Karger, 1997, vol. 34, pp. 21-25 (German).
Schreiber et al., "The risk transfusion-transmitted viral infections", N Engl J Med 1996; vol. 334, pp. 1685-1690.
Spearman, "The Method of 'Right and Wrong Cases' ('Constant Stimuli') Without Gauss's Formulae" Jan. 1908, vol. II, pp. 227-242.
Sterrett, "On the Detection of Defective Members of Large Population", The Annals of Mathematical Statistics, 1957, pp. 1033-1036.
Tuma et al., Development of a Reverse-Transcription PCR (RT-PCR)) for the Detection of HIV-1 RNA in Single Blood Donations.
Yu et al., "Safety of intravenous immunoglobulin with regard to hepatitis C virus", Clin Therapeut 1996; vol. 18, pp. 71-72.
Zerlauth, IQ-PCR: A Quality-Assured and Validated Viral Genome Assay System, Hamostaseologie, 1996, vol. 16, pp. 279-281.
Zulassung Fur Roche's AMPILCOR HIV-1 Monitor Test in den USA als erster Quantitativer AIDS-Test, Hoffmann-LaRoche AG, Jun. 5, 1996, 1 pg.
Schottstedt et al., "Possibilities for the routine screening of all individual donations with respect to HIV-1, HBV and HCV contamination using PCR" Articles on Transfusion Medicine, Jun. 1996, 6 pgs. (English)(D1).
Schottstedt et al., "Moglichkeiten fur das routinemaβige Screening aller Einzelspenden auf Hiv-1-, HBV- und HCV-Kontamination mittels PCR", Beitrage zur Transfusionsmedizin, Jun. 1996, 6 pgs (German)(D1).
International Conference on the Virological Safety of Plasma Derivatives, Conference Program, Nov. 20-22, 1996, 18 pgs. (D2).
Schottstedt, "PCR-Tested Blood Bottles Additional Improvement in the safety of Blood Bottles", Application, Sep. 1996, 4 pgs (English)(D3).
Schottstedt, PCR-getestete Blutkonserven eine weitere Verbesserung in der Sicherheit von Blutkonserven, Application, Sep. 1996, 3 pgs (German)(D3).
Programme of the workshop on 'Nucleic Acid Amplification Tests for the Detection of Blood Borne Viruses', Oct. 31, 1996, 2 pgs. (D5).
List of Participants, EPFA/NIBSC workshop on NAT, Oct. 31, 1996, 12 pgs. (D6).
German Red Cross Donation Service of the German Red Cross Federal Associations, "Increasing safety by testing the blood donations for HIV, HBV and HCV with PCR", Dec. 14, 1995, 5 pgs. (English).
DRK-Blutspendedienst der DRK-Landesverbande Nordrhein und Westfalen-Lippe GmbH, Erhohung der Sicherheit durch Testung der Blutspenden auf HIV, HBV und HCV met der PCR; Dec. 14, 1995, 5 pgs. (German).

* cited by examiner

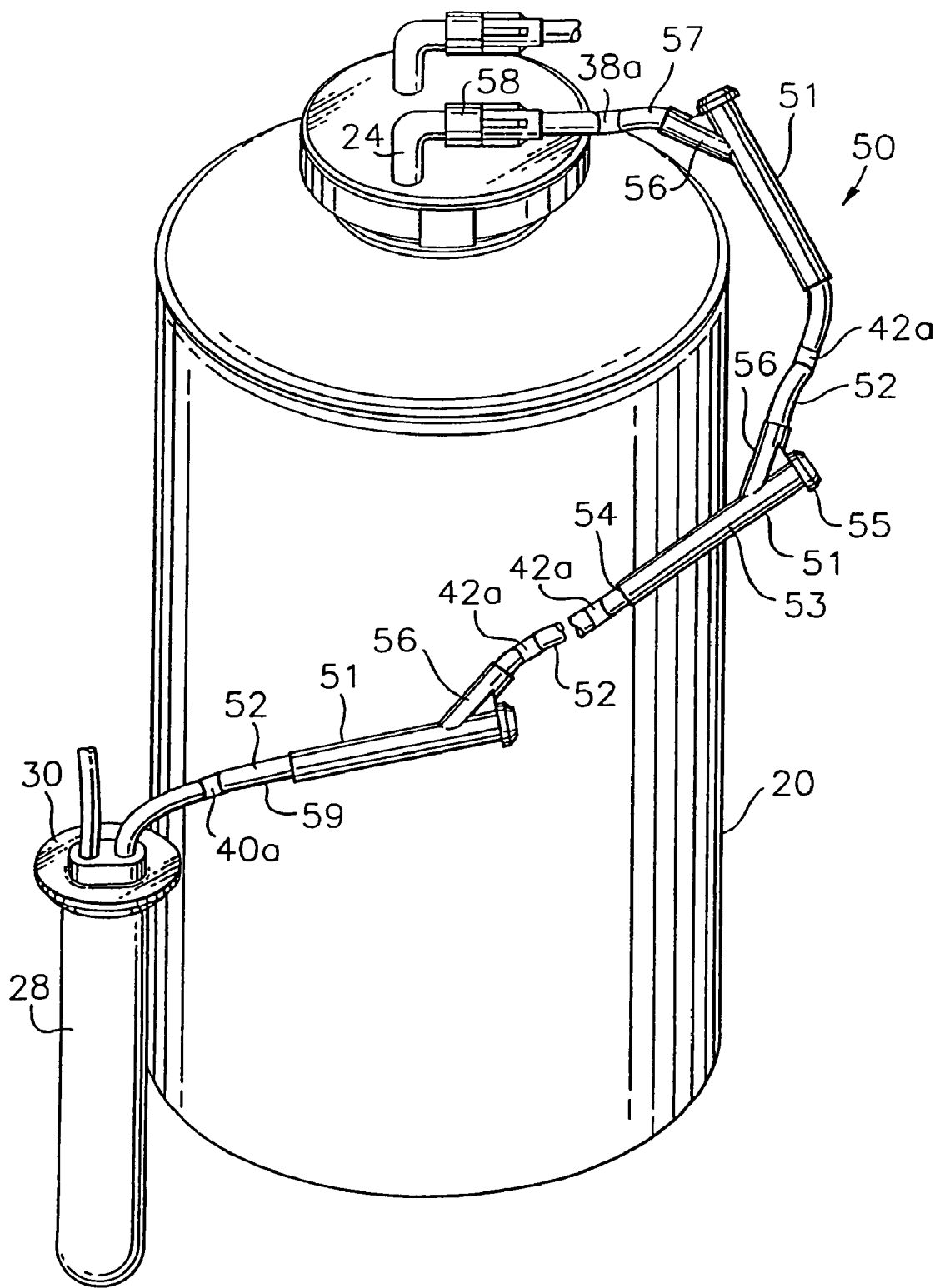

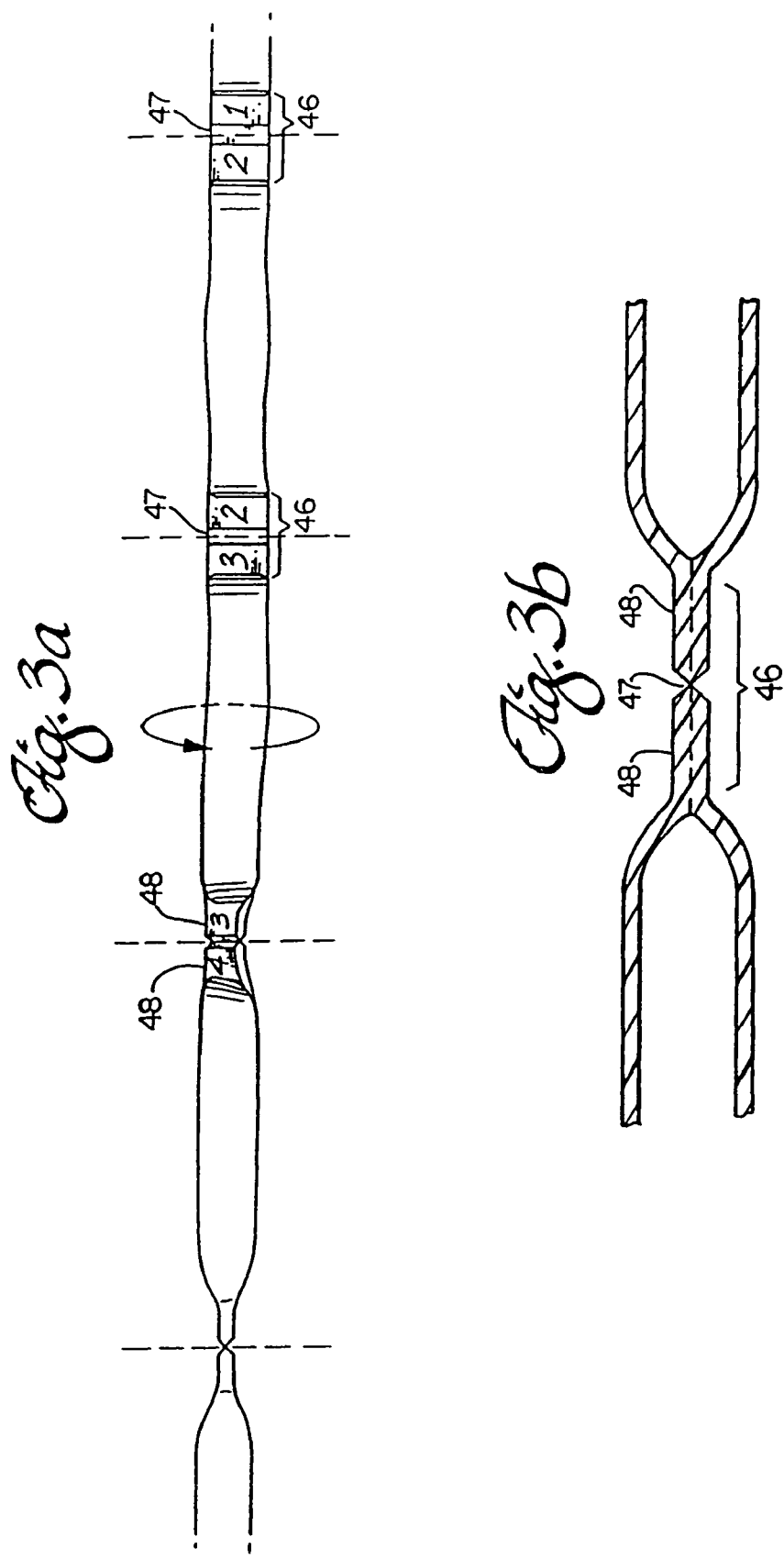

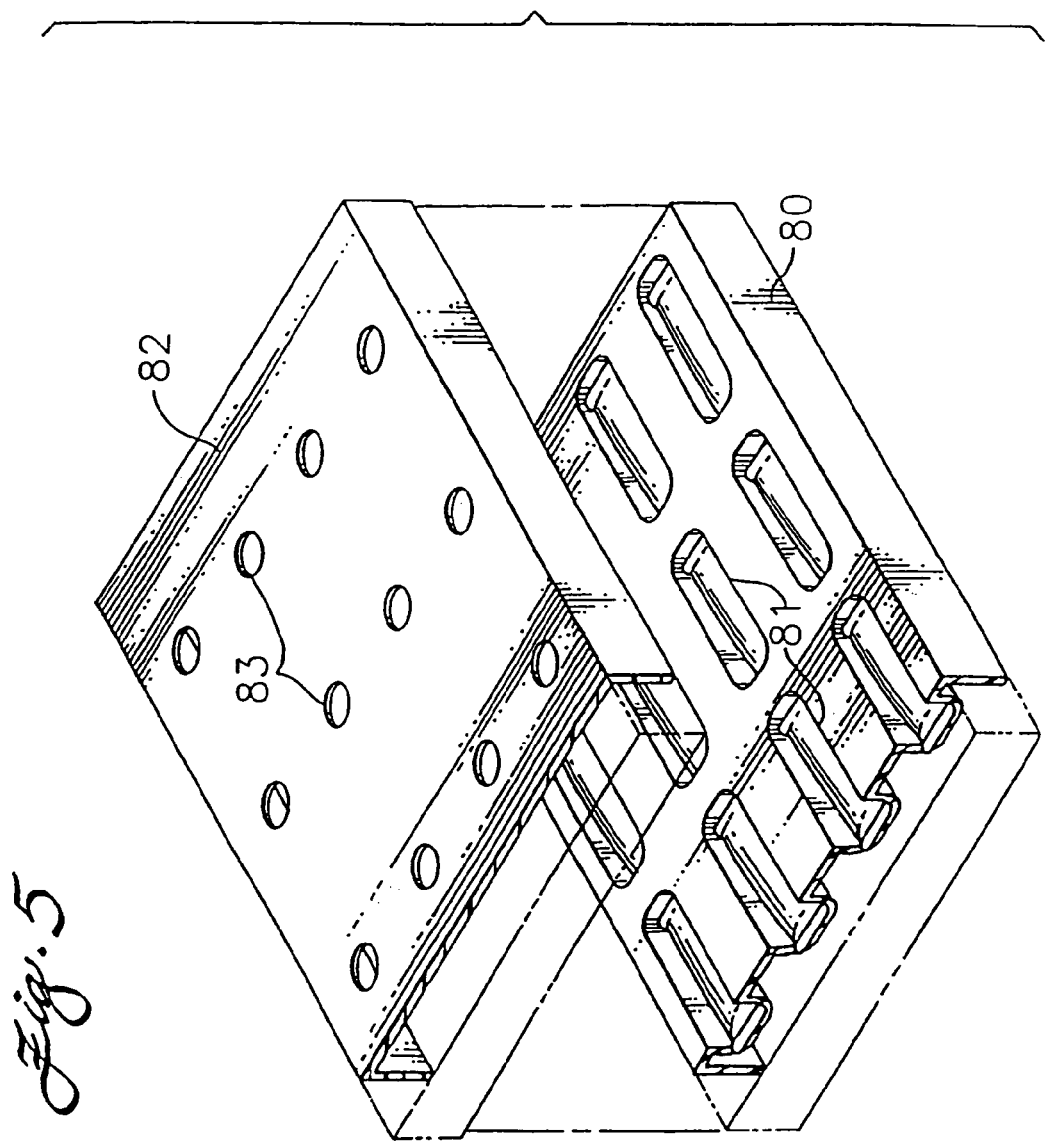

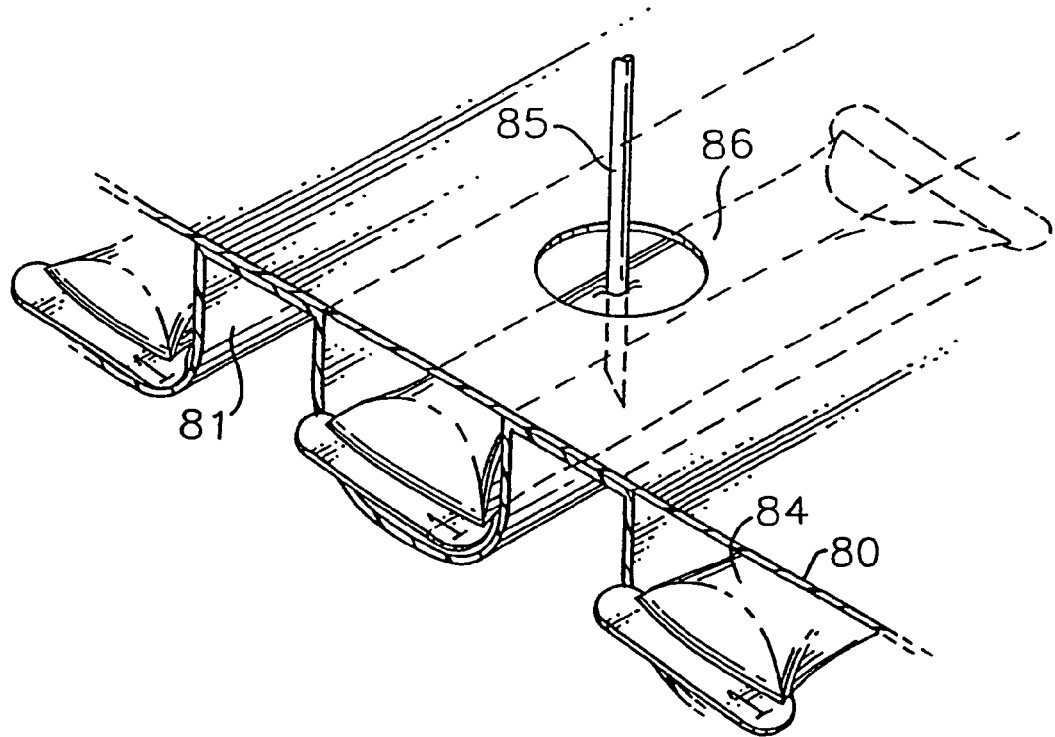

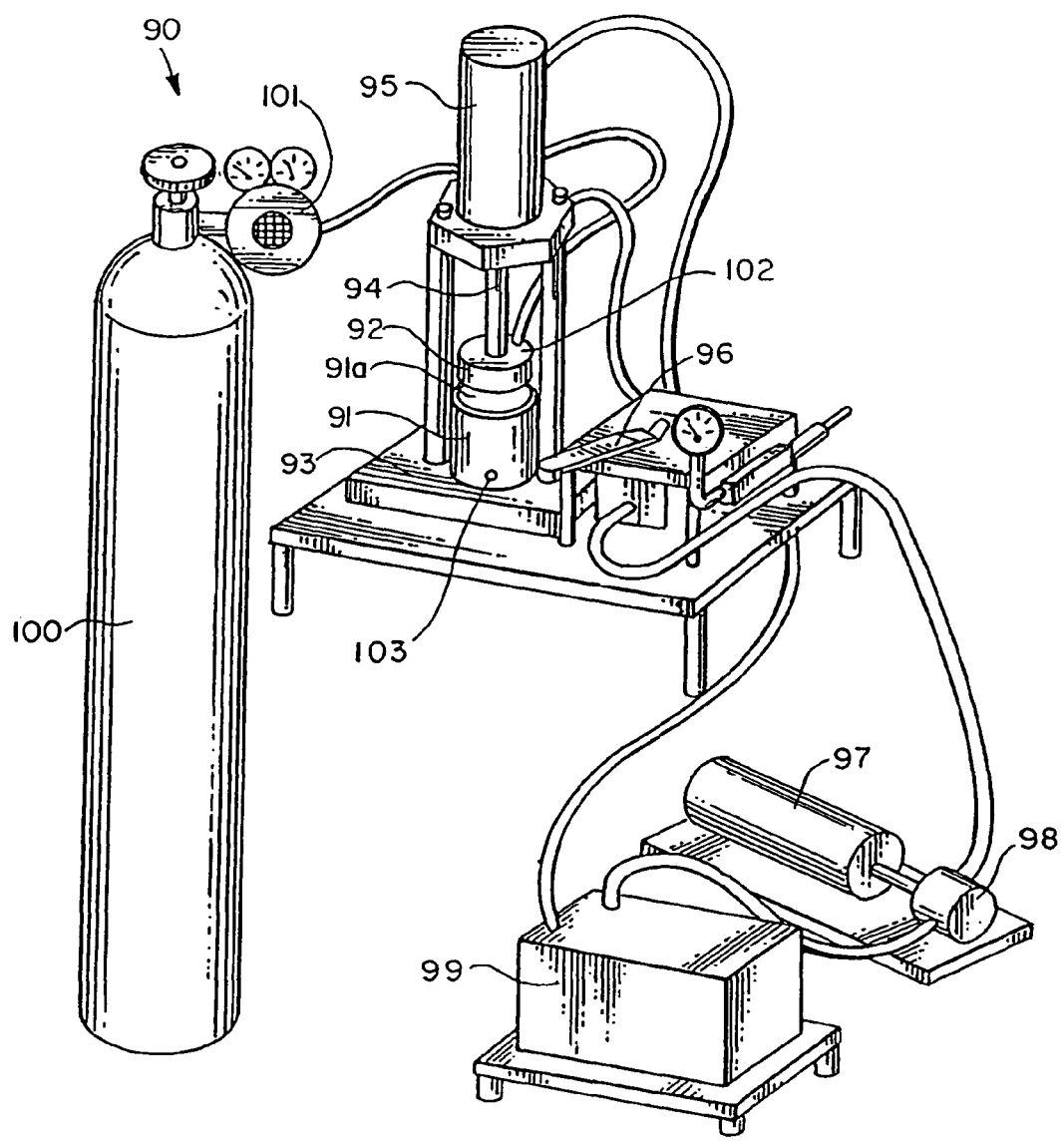

EFFICIENT ALGORITHM FOR PCR TESTING OF BLOOD SAMPLES

CROSS-REFERENCE TO RELATED APPLICATION(S)

This application is a divisional of patent application Ser. No. 10/442,780, filed May 20, 2003 now abandoned which is a divisional of patent application Ser. No. 09/549,477, filed Apr. 14, 2000, now U.S. Pat. No. 6,566,052, which is a divisional of patent application Ser. No. 09/081,926, filed May 20, 1998, now U.S. Pat. No. 6,063,563, which is a divisional of patent application Ser. No. 08/778,610, filed Jan. 6, 1997, now U.S. Pat. No. 5,780,222; which is a continuation-in-part of patent application Ser. No. 08/683,784, filed Jul. 16, 1996, now U.S. Pat. No. 5,834,660; which is a divisional of patent application Ser. No. 08/419,620, filed Apr. 10, 1995, now U.S. Pat. No. 5,591,573.

FIELD OF THE INVENTION

The present invention relates generally to systems and processes for preparing and analyzing samples taken from plasma donations to uniquely identify donations which are virus contaminated. In particular, the invention relates to an apparatus and process for forming individual, separately sealed, and connected containers holding samples of the same plasma as is contained in the donation. The invention also relates to an apparatus and process for forming initial screening test pools from the containers and testing the pools for the presence of a virus in accordance with an algorithm to identify individual contaminated donations in the fewest number of testing cycles.

BACKGROUND OF INVENTION

Blood, plasma, and biological fluid donation programs are essential first steps in the manufacture of pharmaceutical and blood products that improve the quality of life and that are used to save lives in a variety of traumatic situations. Such products are used for the treatment of immunologic disorders, for the treatment of hemophilia, and are also used in maintaining and restoring blood volume in surgical procedures and other treat protocols. The therapeutic uses of blood, plasma, and biological fluids require that donations of these materials be as free as possible from viral contamination. Typically, a serology test sample from each individual blood, plasma, or other fluid donation is tested for various antibodies, which are elicited in response to specific viruses, such as hepatitis C (HCV) and two forms of the human immunodeficiency virus (HIV-1 and HIV-2). In addition, the serology test sample may be tested for antigens designated for specific viruses such as hepatitis B (HBV), as well as antibodies elicited in response to such viruses. If the sample is serology positive for the presence of either specific antibodies or antigens, the donation is excluded from further use.

Whereas an antigen test for certain viruses, such as hepatitis B, is thought to be closely correlated with infectivity, antibody tests are not. It has long been known that a blood plasma donor may, in fact, be infected with a virus while testing serology negative for antibodies related to that virus. For example, a window exists between the time that a donor may become infected with a virus and the appearance of antibodies, elicited in response to that virus, in the donor's system. The time period between the first occurrence of a virus in the blood and the presence of detectable antibodies elicited in response to that virus is known as the "window period." In the case of HIV, the average window period is approximately 22 days, while for HCV, the average window period has been estimated at approximately 98 days. Therefore, tests directed to the detection of antibodies, may give a false indication for an infected donor if performed during the window period, i.e., the period between viral infection and the production of antibodies. Moreover, even though conventional testing for HBV includes tests for both antibodies and antigens, testing by more sensitive methods have confirmed the presence of the HBV virus in samples which were negative in the HBV antigen test.

One method of testing donations, which have passed available antibody and antigen tests, in order to further ensure their freedom from incipient viral contamination, involves testing the donations by a polymerase chain reaction (PCR) method. PCR is a highly sensitive method for detecting the presence of specific DNA or RNA sequences related to a virus of interest in a biological material by amplifying the viral genome. Because the PCR test is directed to detecting the presence of an essential component of the virus itself its presence in a donor may be found almost immediately after infection. There is, theoretically therefore, no window period during which a test may give a false indication of freedom of infectivity. A suitable description of the methodology and practical application of PCR testing is contained in U.S. Pat. No. 5,176,995, the disclosure of which is expressly incorporated herein by reference.

PCR testing is, however, very expensive and since the general donor population includes a relatively small number of PCR positive donors, individual testing of each donation is not cost effective or economically feasible. Hence, an efficient and cost-effective method of testing large numbers of blood or plasma donations to eliminate units having a viral contamination above a pre-determined level is required.

One method of testing a large number of plasma donations is to pool a number of individual plasma donations. The pool is then PCR tested and the individual donations comprising the pool are either retained or disposed of, depending on the outcome of the PCR test. While reducing the number of PCR tests, and the costs associated therewith, this method results in a substantial waste of a significant portion of virus free donations. Since only a single donation with a viral contamination above a pre-determined level will cause a pool to test PCR positive, the remaining donations that contribute to a pool may well be individually PCR negative. This result is highly probable given that a relatively small number of PCR positive donors exist in the general donor population. In the conventional pooling approach, all donations comprising the pool are disposed of upon a PCR positive result, including those donations that are individually PCR negative.

In addition, plasma donations are often frozen soon after they are received. When samples of individual plasma donations are needed for pooling, each donation must be thawed, an aliquot of the blood or plasma removed from the donation, and the donation must then be refrozen for preservation. Multiple freeze-thaw cycles may adversely affect the recovery of the RNA or DNA of interest as well as the proteins contained within the plasma, thus adversely affecting the integrity of the PCR test. Moreover, each time an aliquot of individual plasma donations is withdrawn to form a pool, the donation is subject to contamination, both from the surrounding environment, and from the apparatus used to withdraw the aliquot. Further, if the donation contains a virus, it can contaminate other donations. In order to avoid introducing viral contaminants into an otherwise viral free donation, the sample taking apparatus must be either sterilized after each individual use, or used for taking only a single aliquot from a single individual donation and a new sample taking apparatus used for taking an aliquot from a subsequent individual donation. Either of these methods involves considerable expense and is quite time consuming.

Accordingly, there is a need for a process and system for obtaining multiple blood or plasma samples from individual donations such that particular samples may be pooled without contaminating the remaining samples. It is also desirable that the process and system is able to form such pools in a fast and efficient manner, without contaminating either a clinical testing lab technician or the testing laboratory environment.

In addition, it is desirable that the process and system provide for efficient and cost-effective testing of the blood or plasma donations to identify only uniquely PCR positive donations in the fewest possible number of testing cycles.

SUMMARY OF INVENTION

There is, therefore, provided in the practice of this invention a cost-effective and efficient process for preparing and testing samples from a multiplicity of blood or plasma donations to uniquely identify donations which are infected with virus as well as systems and devices for practicing the process.

The process of the present invention results in blood and plasma products being substantially safer because one can readily test for virus contamination in the blood or plasma supply directly. Cost-effective, high-sensitivity testing can be performed immediately, and contaminated donations identified, without regard to an infectivity window period.

In one embodiment of practice of the present invention, the process comprises the steps of providing a blood or plasma donation in a collection container. A flexible collection segment is connected to the container and is open to the inside of the container. The collection segment is filled with blood or plasma from the collection container, and a portion of the collection segment is sealed at both ends. The sealed portion of the collection segment is removed from the container and, either before or after the sealed collection segment portion is removed, a plurality of spaced-apart seals are provided at intervals along the length of the collection segment between the sealed ends. The segment portions in the intervals between adjacent seals define containers, wherein each such container contains a plasma or blood sample, and wherein the intervals between the seals provide a sufficient volume in each such container for the planned testing.

In a more detailed embodiment of the present invention, individual plasma donations are collected in a plasma collection bottle which has a testing container connected thereto by a flexible hollow tubing segment. After being filled with a donor's plasma the plasma bottle is tipped so as to transfer plasma to the testing container and the flexible tubing segment, thereby filling the tubing segment. The tubing segment is sealed at spaced-apart intervals along its length, the tubing segment portions in the intervals between the seals define pouches each of which contains a sample of the plasma donation. The tubing segment, which has been converted into a series of pouches, is then disconnected from the plasma collection bottle and frozen until needed for testing.

In an additional aspect of the present invention, the hollow tubing segment comprises a series of linked-together Y-sites, including an injection site provided on one leg of the Y, and where each branch leg of a particular Y-site which does not include an injection site is connected to the base of the next Y-site in the chain by a flexible plastic tubing segment. Spaced-apart heat seals are formed along the length of each flexible plastic tubing segment separating the Y-sites.

In a further aspect of the present invention a device for providing multiple heat seals along the length of the tubing segment filled with the blood or plasma donation comprises first and second opposed seal platens. Each seal platen includes a plurality of spaced-apart raised portions along its length alternating with recessed portions. The raised and recessed portions on the first platen are in registry with corresponding raised and recessed portions on the second platen. The opposed seal platens are moved together onto a plastic tubing segment filled with the blood or plasma donation to form heat seals on those portions of the tubing segment compressed between the raised portions and to form chambers defined by opposed recessed portions. The heat seals define a plurality of individual and sequential pouches therebetween and each chamber, defined by each closed pair of recessed portions, is configured to house a pouch.

In particular, a device for providing multiple heat seals along the length of the tubing segment filled with a blood or plasma donation is configured to be mounted on a commercially available heat seal apparatus, as an after-market modification.

In yet a further embodiment of the invention, a system for collecting and preparing plasma samples for testing comprises a plasma collection container and a hollow plastic tube connected to the container, each of which are constructed of plastic and each of which contain a coded indicia molded into the plastic. The coded indicia is disposed along the major axis of the tubing segment and the code repeats at spaced-apart intervals so that the tubing segment can be provided with a plurality of spaced apart seals along its length to thereby define pouches between the seals. The code intervals of the indicia correspond to the intervals of the pouches, so that each pouch will contain at least one cycle of the code.

To begin the testing process of the present invention, a first pouch is removed from each of a group of tubing segments corresponding to a plurality of separate plasma donations. A portion of the contents of each such first pouch is withdrawn and the contents formed into a pool in a container.

In an exemplary embodiment of the present invention, the first pool is tested for a viral indication. When the first pool tests positive for a viral indication, a next, or second, sequential pouch is removed from each of the tubing segments that were used to form the first pool. The second pouches are divided into two approximately equal subgroups, and the contents of one of the subgroup pools is tested for the presence of a specific virus. When the tested subgroup pool tests negative for the virus, a further sequential pouch is removed from corresponding tubing segments used to form the untested subgroup. The pouches are divided into two approximately equal next generation subgroups, and the contents of the subgroup pouches are formed into pools. One of the next generation subgroup pools is tested for a viral indication.

When the tested subgroup pool tests positive for such viral indication, a pouch is removed from corresponding tubing segments used to form the tested subgroup. The process is iterated, with each positive pool being further subdivided into successively smaller subgroups, with each of the successive subgroups comprising a fraction of the samples of the preceding positive subgroup, until the final pouch corresponding to a single plasma donation is identified.

In a further embodiment of the present invention, an additional process for testing a multiplicity of plasma donations to uniquely identify donations having a positive viral indication in a single PCR testing cycle includes the steps of defining an n-dimensional grid which defines internal elements at the intersections of each of the n-dimensions of the grid. A sample from each of a number of plasma donations is mapped to a corresponding element of the grid, with each sample being defined by a matrix notation, $X_{res}$, where the subscript of the matrix element notation defines dimensional indices of the grid. Aliquots are taken from each sample of each of the plasma donations and formed into subpools. Each subpool includes an aliquot of all plasma donation samples in which one of the dimensional indices is fixed. The subpools are all tested at once, in a single PCR testing cycle, and the dimensional indicia of each subpool which tests positive is evaluated in accordance with a reduction by the method of minors, thereby unambiguously identifying a unique element defined by the dimensional indicia of each positive subpool, and thus unambiguously identifying a uniquely positive sample.

BRIEF DESCRIPTION OF THE DRAWINGS

These and other features, aspects, and advantages of the present invention will be more fully understood when considered with respect to the following detailed description, appended claims, and accompanying drawings, wherein:

FIG. 2a is a semi-schematic perspective view of a tubing segment connected between a plasma donation bottle and sample container and including a series of linked-together Y-sites in accordance with the present invention;

FIG. 3a is an enlarged top plan view of a portion of the tubing segment shown in FIG. 2 showing additional details of the seals which separate the pouches;

FIG. 3b is a semi-schematic cross-sectional view of a tubing segment seal;

FIG. 5 is a semi-schematic perspective view of a sampling plate and cover provided in accordance with the present invention;

FIG. 6 is a semi-schematic partial cross-sectional view of a plasma pouch contained in a sampling plate sample well provided in accordance with the present invention;

FIG. 7 is a semi-schematic perspective view of a device provided in accordance with the present invention for crushing sample pouches and expressing the fluid samples container therein into a pool;

DETAILED DESCRIPTION OF THE INVENTION

The present invention relates to systems, processes and devices useful for testing blood or plasma donations to detect those specific donations which have a viral contamination above a pre-determined level. Such contaminated donations are then disposed of to thereby prevent their incorporation into the raw material stream for pharmaceutical products or their transfusion into human patients. The viral detection tests used in accordance with practice of the present invention can be any that directly detect a virus instead of antibodies elicited in response to the virus. The tests include polymerase chain reaction (PCR) tests and other tests which are sufficiently sensitive to directly detect a virus even after pooling samples from multiple donations.

In one embodiment of practice of the present invention, a plurality of separate blood or plasma donations are provided. A blood or plasma sample is drawn from each donation into a corresponding flexible, hollow tubing segment. A plurality of spaced-apart seals are provided at intervals along the length of the tubing segment, so that segment portions in the intervals between seals define pouches where each pouch contains a blood or plasma sample. As is discussed below in greater detail, a unique methodology is provided in accordance with the present invention for testing plasma samples from the pouches after the samples are formed into pools to thereby efficiently and effectively detect and isolate any such blood or plasma donation which is contaminated with virus.

Figure 1:
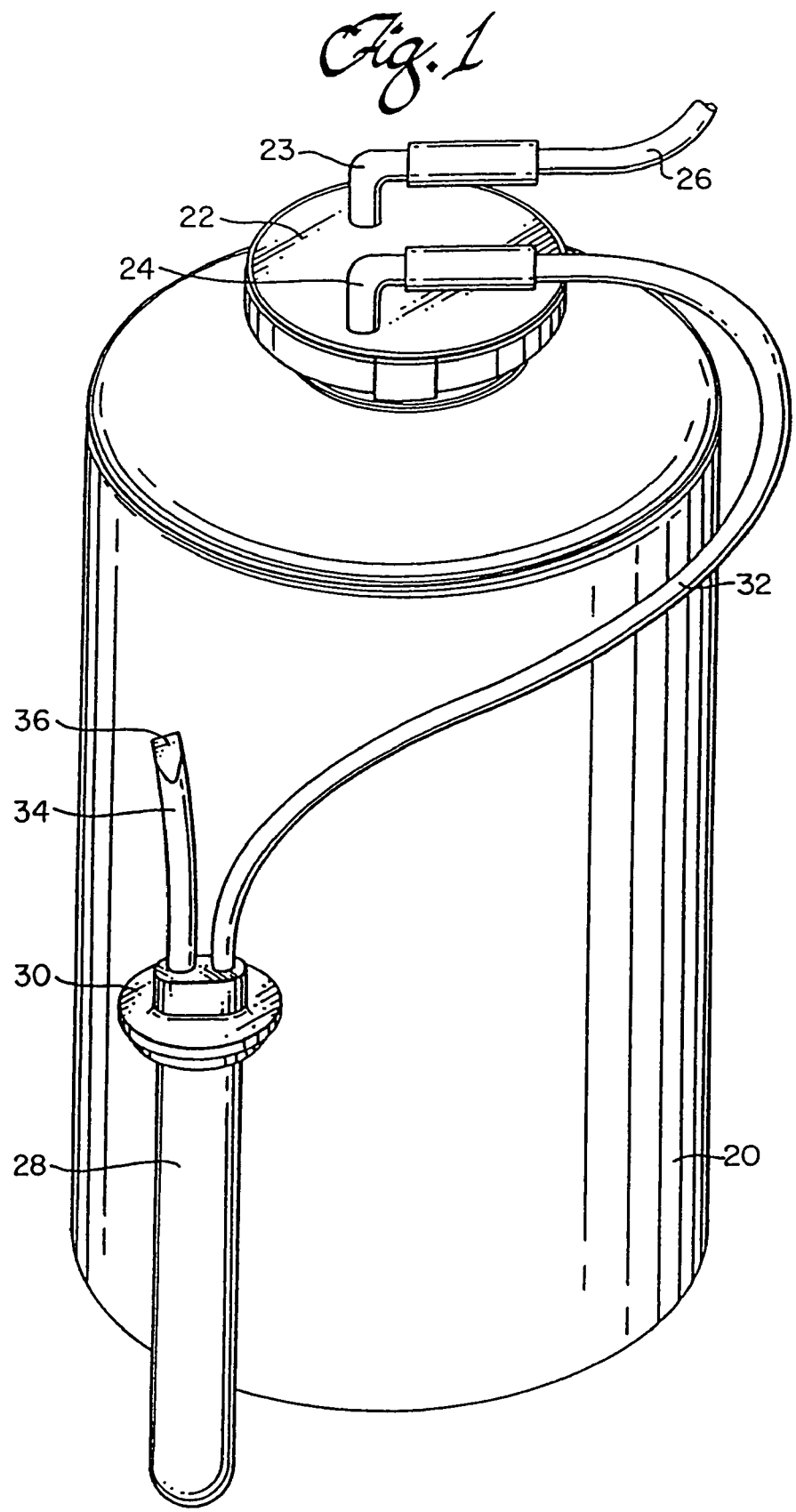
FIG. 1 is a semi-schematic perspective view of one example of a plasma donation bottle and sample container attached by a tubing segment useful in the practice of the present invention.

Turning to FIG. 1, an exemplary embodiment of a system provided in accordance with practice of the present invention for effecting the sampling process is shown. The system includes a standard plasma donation container 20, constructed of a nonreactive material such as polyvinyl chloride (PVC). The donation container 20 includes a cap 22 having two hollow elbow shaped fittings 23 and 24, respectively, attached to the top surface thereof The fittings communicate with the interior of the donation bottle through orifices provided in cap 22 for such purpose. A flexible hollow filler tube 26, constructed of a biologically neutral material, such as PVC plastic, is connected at one end to the elbow fitting 23 and connected at the other end to, for example, a needle which is inserted into a donor in order to procure a donation. In the illustrated embodiment, a test container 28, is also provided, for collecting a sample from the donation to be serology tested. The test container 28 is generally test tube shaped and is also constructed of a biologically nonreactive material. The test container 28 includes an integral cap member 30 through which orifices are provided in order to communicate with the interior of the test container.

A flexible hollow tubing segment 32, constructed of a biologically nonreactive plastic material, is connected between the cap member 30 of the test container 28 and the hollow elbow fitting 24 of the plasma donation container cap. The tubing segment 32 is connected to the cap member 30 in a manner such that fluid passing through the tubing segment will enter the test container 28 through an orifice provided in the cap member 30 for such purpose. The tubing segment 32 may be friction fit into said orifice, sonically welded thereto, or otherwise attached in a coaxial relationship with the orifice by techniques well understood by those skilled in the art.

A second orifice may also be provided in the cap member 30, to which a vent tube 34 is connected in a manner similar to tubing segment 32. The vent tube is typically no more than one to two inches in length, and is typically terminated with an inserted, friction fit bacteria excluding filter 36.

In an exemplary embodiment, a blood or plasma donation is withdrawn from a donor and collected in the plasma donation container 20 for subsequent storage until needed. In the case of a plasma donation, blood is typically withdrawn from a donor and passed through a continuous centrifuge apparatus, wherein red blood cells are centrifuged out from the supporting plasma fluid and returned to the donor. The plasma is then collected.

After a plasma donation is taken from a donor and the donation container 20 is filled, the donation container is tilted so as to raise the fluid level over the elbow fitting 24 connected to the tubing segment 32. Plasma enters the tubing segment, flows through the tubing segment, and fills the test container 28. During filling, air trapped within test container 28 escapes through the vent tube 34, allowing the test container to be filled completely. The bacteria excluding filter 36 filters out any bacteria in the returning air, thus preventing contamination of the sample by the surrounding environment. After the test container is filled, plasma from the donation is allowed to fill the tubing segment 32.

Figure 2:
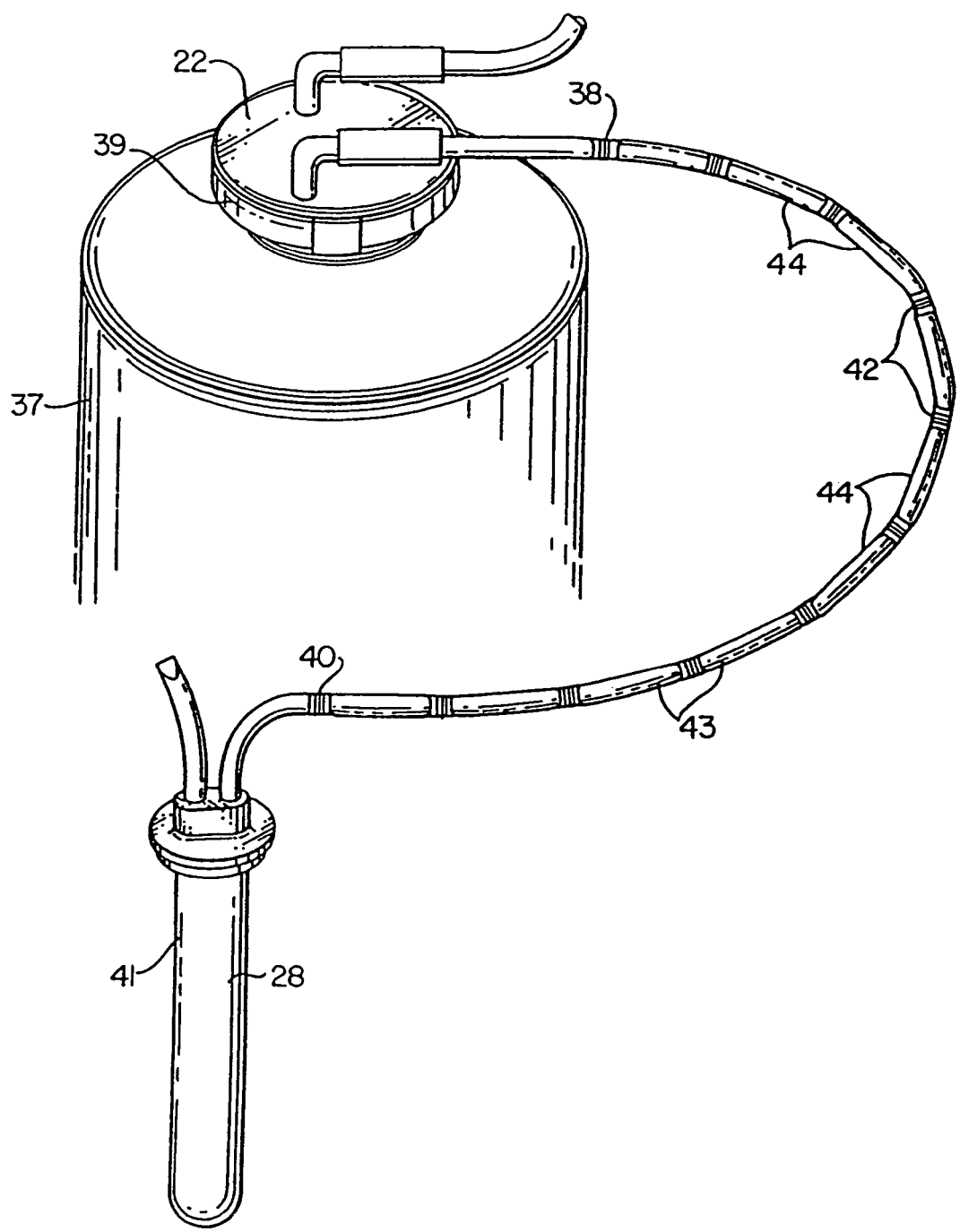
FIG. 2 is a semi-schematic perspective view of a tubing segment connected between a plasma donation bottle and sample container and divided into pouches in accordance with the present invention.

Turning now to FIG. 2, after the plasma sample from the donation is drawn into the tubing segment 32, the tubing segment is sealed by a heat weld 38 or other suitable sealing means such as a sonic weld, at a location proximate to the tubing segment's connection to the plasma donation container. A further heat seal 40 is applied to the tubing segment at a location proximate to the segment's connection to the test container 28. An elongated hollow tube, closed off at both ends, and containing a quantity of the plasma donation is thus provided.

The filled portion of the tubing segment 32 is removed from the plasma donation and test containers by cutting the tubing segment away through the center of the seals, 38 and 40. The separate plasma donation container is then removed for freezing and storage, while the separated test container is removed to a laboratory for serology testing. Typically, the contents are tested for various antibodies, which are elicited in response to specific viruses, such as hepatitis C (HCV), or HIV-1 and HIV-2.

Additional seals 42 are also provided at spaced-apart intervals along the length of the tubing segment, to define sequential individual and connected pouches, each suitably comprising a hollow tubing segment portion 44. Each such portion 44 contains a particular quantity of blood or plasma needed for the specific generation pool to be formed. For example, for pouches to be formed for PCR testing, approximately 0.02 to 0.5 ml of blood or plasma from the host donation may be sealed.

The tubing segment is sealed in a manner to provide from 5 to 15, individual and connected pouches. Sealing, to define the pouches, may be done either after the tubing segment has been removed from between the plasma donation container and the serology test container or preferably is done while the tubing segment is still attached to the plasma donation container, in order to avoid hydrostatic pressure build-up. Sealing may be done by any known method, such as thermo-compression sealing (heat sealing), sonic welding or the like, so long as the length of the region compressed and sealed is sufficient to permit the connected pouches to be separated from one another by cutting through the center of the seal without violating the integrity of the pouch on either side, as indicated more clearly in FIGS. 3a and 3b. A second embodiment of the tubing segment adapted to be subdivided into blood or plasma sample-containing aliquot portions is depicted in FIG. 2a which is a semi-schematic perspective view of a collection tubing segment embodiment connected between a plasma donation bottle 20 and sample container 28 and divided into aliquot-containing portions in accordance with the present invention.

The collection tubing segment 50 is connected between the cap member 30 of the test container 28 and the hollow elbow fitting 24 of the plasma donation container cap. The tubing segment 50 suitably comprises a plurality of Y-sites 51 connected together in series by flexible, hollow, medical-grade plastic tubing segments 52. The Y-sites 51 are of the type commonly adapted for connection to an intravenous infusion set and include a cylindrical body portion 53 with a flow path defined therethrough, having an outlet 54 at one end of the flow path and an access site 55 at the other end. A branch port 56 is provided along the body 53 of the Y-site and includes a fluid path which is in communication with the fluid path through the body 53.

One Y-site is connected to the next by solvent bonding a flexible, hollow, medical-grade plastic tube 52 between the outlet port 54 on the bottom of one Y-site to the branch port 56 of the next Y-site in the series. An initial hollow entry tube 57 is solvent bonded to the branch port of the initial Y-site in the series. The initial entry tube 57 is connected, in turn, to the elbow fitting 24 of the plasma donation container cap. Connection may be made by friction-fitting the initial entry tube 57 onto the elbow fitting 24, sonically welding the tube thereto, or otherwise attaching the tube in a coaxial relationship with the fitting by techniques well understood by those skilled in the art. Moreover, the initial entry tube 57 may terminate in a standard luer-type fitting 58 which would allow the series-connected Y-sites to be removably connected to a donation container which was provided with a mating luer-type connector at the end of the elbow 24.

In like manner, the terminal Y-site is fitted with a flexible, hollow terminal exit tube 59 which is solvent-bonded to the terminal Y-site at its outlet port. This tube may also be connected to a standard luer-type fitting at its distal end.

In a manner similar to that described in connection with the first embodiment, after a plasma donation is taken from a donor and the donation container 20 is filled, the donation container is tilted so as to raise the fluid level over the elbow fitting 24 connected to the entry tube segment 57. Plasma enters the tubing segment and flows through the series-connected Y-sites, entering each Y-site through its branch port 56 and flowing into the next Y-site from the preceding Y-site's outlet port 54. Plasma is decanted until the test container 28 is filled. After the test container is filled, the donation is further decanted until the series-connected Y-sites comprising the tubing segment 50 are also filled.

After the plasma sample from the donation is drawn into the tubing segment 50, the terminal exit tubing segment 59 is closed off by a heat seal or weld 40a or other suitable sealing means such as a sonic weld at a suitable location along its length proximate to the terminal exit tubing segments connection to the test container 28.

The filled tubing segment 50 is removed from the test container by cutting the terminal exit tubing segment 59 away from the test container through the center of the seal 40a. Alternatively, if the tubing segment 50 terminates in a luer-type connector, the tubing segment 50 is removed from the test container 28 by disconnecting the luer. A second heat seal 38a is applied to the initial entry tubing segment 57 at a location along its length proximate to the initial segment's connection to the donation container 20. The filled portion of the tubing segment 50 is removed from the plasma donation by cutting the initial entry segment 57 away through the center of the seal 38a, or by disconnecting the luer-type fitting 58, if such is provided. An elongated, hollow, articulated tube, closed off at both ends and comprising a plurality of Y-sites linked-together in series, is thus provided. Each of the linked-together Y-sites contains an aliquot of the blood or plasma donation.

As will be described in greater detail below, the tubing segments connecting a preceding Y-site's outlet port to a subsequent Y-site's branch port are also provided with heat seals 42a to define sequential, individual, and connected sample aliquots, each suitably comprising an individual Y-site. Each such Y-site contains a particular quantity of blood or plasma needed for a specific generation pool to be formed. Sealing to isolate each Y-site may be performed either after the tubing segment 50 has been removed from the plasma donation container or may be performed while the tubing segment is still attached. Preferably, sealing to isolate the Y-sites is performed while the tubing segment 50 still attached to the plasma donation container so that the volume reduction caused flattening a portion of the tubing during the sealing process does not cause a build-up in the internal hydrostatic pressure of the sample. When the tubing segment 50 remains connected to the plasma donation container, excess fluid created by the volume reduction of the tubing created by the heat seals is allowed to be expressed back into the donation container. Excess hydrostatic pressure, which may lead to dangerous spurting during sample extraction, is thus safely relieved.

Sealing may be performed by any known method, such as thermo-compression sealing (heat sealing), sonic welding or the like, so long as the length of the region which is compressed and sealed is sufficient to permit the connected Y-sites to be separated from one another by cutting through the center of the seal without violating the integrity of the tubing segment on either side of the seal.

Turning now to FIGS. 3a and 3b, in a preferred embodiment, the seal between pouches (42 of FIG. 2) and/or Y-sites (51 of FIG. 2a) includes a flat pad area 46, including a central narrow portion 47 through which the seal is cut or torn in order to separate the connected pouches. Cutting is done through the central portion in order to insure that each separated pouch remains sealed at compressed tab portions 48 at either end after separation. The length of the seal pad may be made greater or smaller, depending on the chosen separation method. Separation may be done by use of a scalpel, a guillotine cutter, or a simple pair of scissors.

Figure 4:
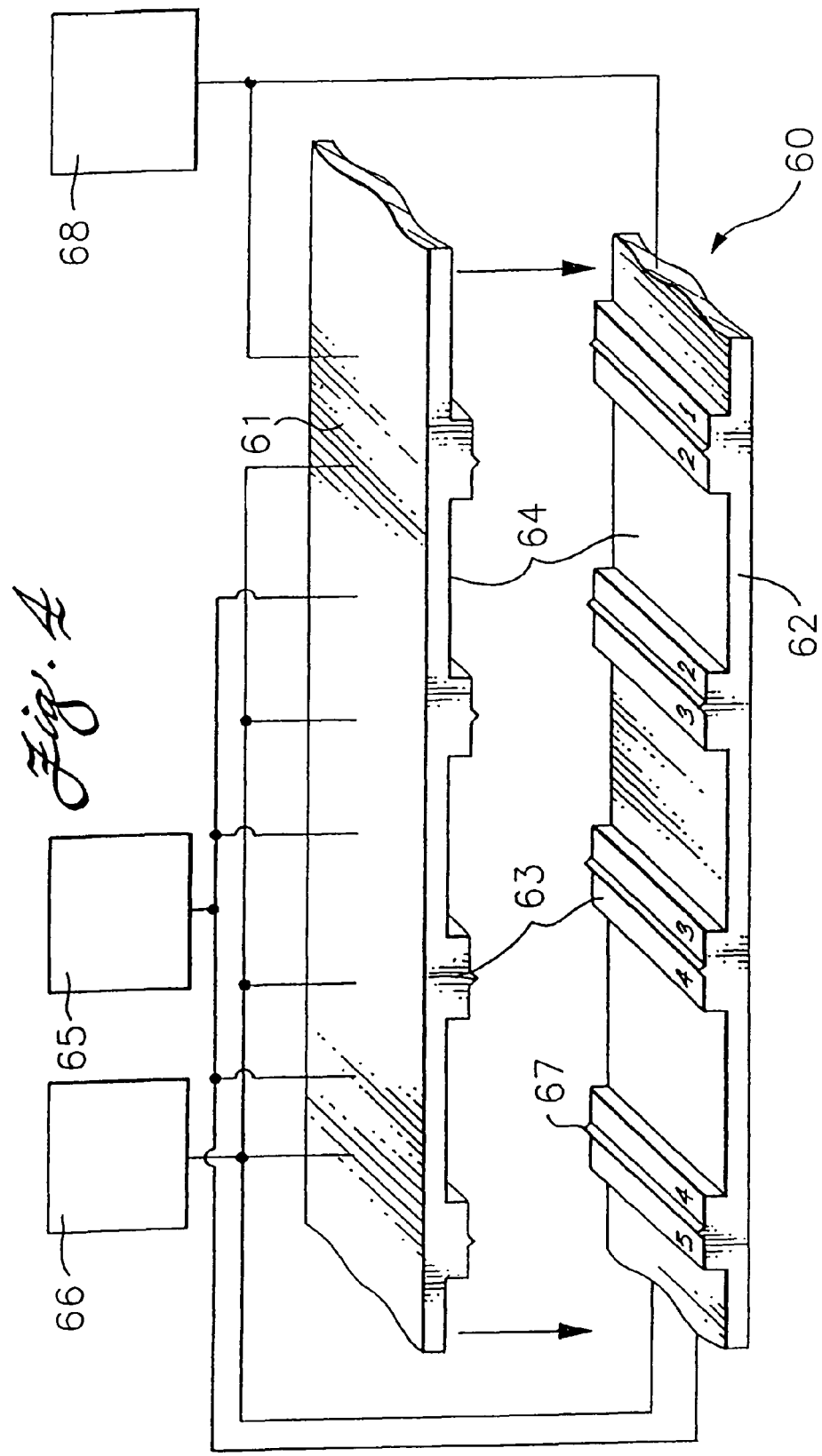
FIG. 4 is a semi-schematic perspective view of a device provided in accordance with practice of the present invention for sealing a tubing into individual pouches.

Turning to FIG. 4, an exemplary embodiment of a sealing device 60, useful for providing pouches of specific desired sizes, including means to easily separate the pouches and identify their sequence number along a segment, is shown. The sealing device 60 suitably comprises opposed first and second platens 61 and 62, respectively, each including a plurality of raised, seal head portions 63, arranged in a spaced apart relationship on the opposing surfaces of the platen. The sealing device 60 is preferably constructed such that the raised seal head portions 63 are movable along their respective platens such that the spacing from one raised seal head portion to another may be varied. The raised seal heads 63 may be arranged along the platen such that the distance between successive seal heads is made progressively smaller so that sealing is performed along the length of a tubing segment at progressively closer spaced intervals. Thus, sample pouches of progressively smaller size and, therefore, progressively smaller volume content may be formed by moving pairs of opposed seal heads along their respective platens to a desired location.

In order to form multiple heat seals along the length of the plastic tubing segment filled with a blood or plasma sample, the tubing segment is placed within the sealing device 60 between the upper and lower sealing platens 61 and 62, respectively. The opposed platens are brought into proximity with one another, thus compressing and sealing the tubing segments. As depicted in FIG. 4, the plurality of spaced-apart, extended or raised seal head portions 63 along the length of each platen alternate with recessed portions 64. As the opposed platens are moved together to form heat seals on those portions of a plastic tubing segment filled with a blood or plasma sample compressed between the raised seal head portions 63, chambers are formed by the opposed recessed portions 64. The chambers are provided in order to accommodate those portions of the tubing segment which are not to be compressed but, rather, to be formed into pouches. Each chamber defined by each closed pair of recessed portions is configured to house a pouch.

A heater 65 is configured to heat each of the seal head portions of the platen in order for opposed raised portions to form a heat seal on the tubing segment when the sealing device is closed. The heater 65 may be any one of well known heater types such as radiant heaters, induction or resistance heaters, or the like. The heater 65 is preferably connected directly to each of the raised seal heads 63 to heat the raised portions without unduly heating the recesses. If desired, insulation can be provided to reduce heat transfer between the raised portions and the recesses. In an exemplary embodiment, a cooling device 66, such as cooling or radiator fins, a moving air flow, or a cold finger, may also be connected to the sealing device 60. The cooling device 66 is connected directly to each of the recessed portions 64 so that the chambers defined when opposed recessed portions move together are maintained at a low temperature. Blood or plasma samples contained in pouches formed within the chamber during the seal process are thus not damaged by the high temperatures of the heat seal.

The narrow area (47 of FIG. 3b) through approximately the center of the seal is formed by an elongated ridge structure 67 provided down the center of the extended seal head portion 64 of the seal platens. As the tubing segment is squeezed between the upper and lower sealing heads, the ridge 67 forces an indentation on the top and bottom surface of the seal portion. The indentations narrow the plastic material comprising the center the seal, thus making it easy to separate.

In one embodiment of the invention, the ridge 67 may be serrated in order to provide perforations disposed in a direction orthogonal to the major axis of the tubing segments. The perforations allow the individual and connected pouches to be removed from one another without the danger inherent with cutting with a sharp object of violating the integrity of a pouch by inadvertently cutting through to the sample containing area. The perforations are preferably provided during the seal process by providing the seal heads with serrations. Alternatively, perforations may be provided shortly thereafter by use of a separate perforating jig or die.

Means 68 are also provided to open and close the sealing device 60 in order to compress the seal platens together and thus form seals along the length of the tubing segment. Such means are well known in the art and may suitably comprise a manual apparatus which opens and closes, such as a lever handle attached to one support frame and which moves the frame against, for example, a hinge. Other suitable arrangements may include vertical guides, springs, or hydraulically operated piston presses, or other common mechanical, electrical, or hydraulic presses.

Figure 4A:
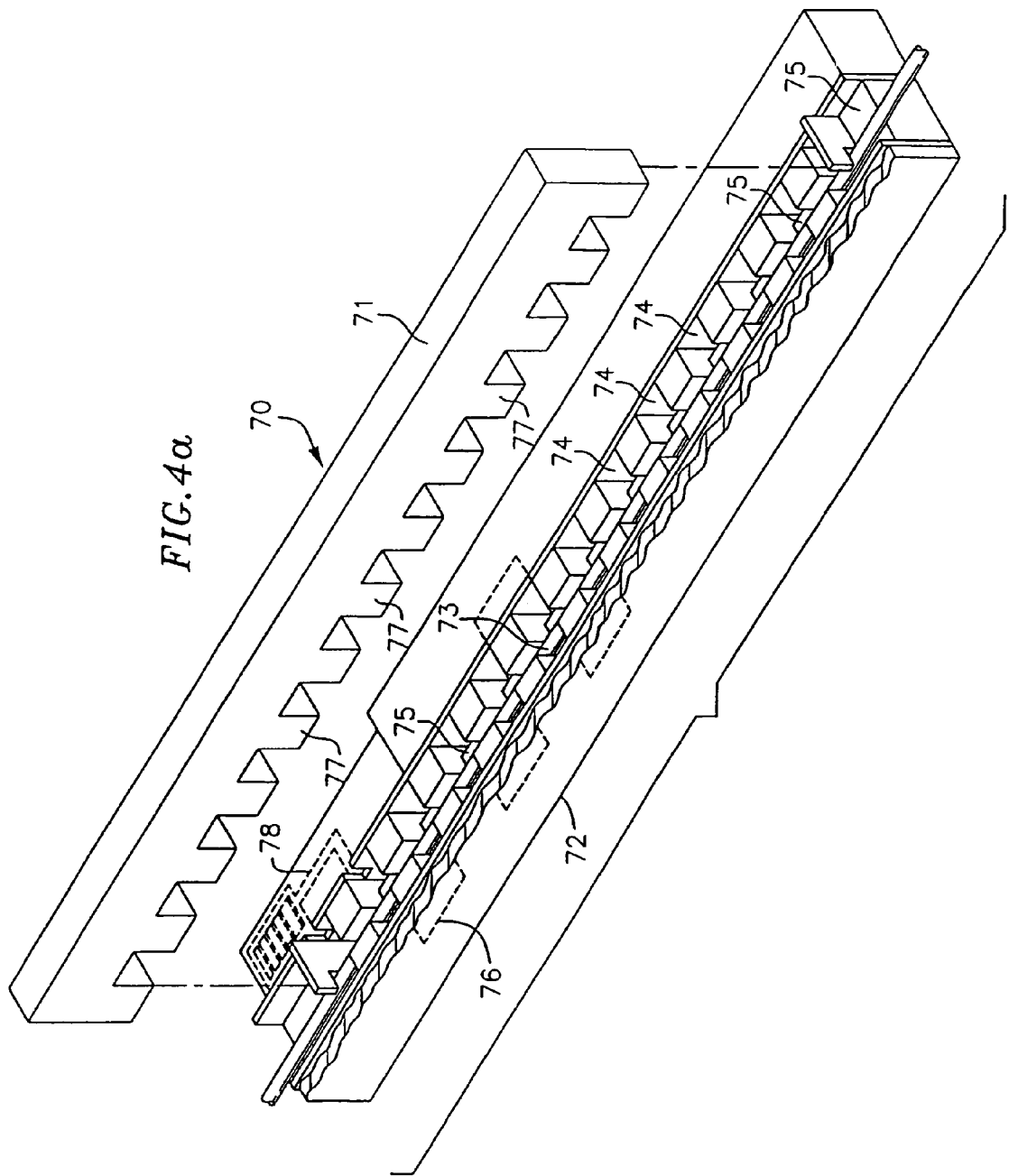
FIG. 4a is a semi-schematic perspective view of a top and bottom platens of a heat sealing device provided in accordance with practice of the present invention for mounting onto a commercially available heat sealer.

Turning now to FIG. 4a, there is depicted in semi-schematic view, a specific embodiment of a sealing device 70, useful for providing thermo-compression heat seals at uniform, spaced-apart intervals, so as to form pouches of specific desired sizes, or to isolate linked-together Y-sites into individual sample-containing aliquots. The sealing device 70 suitably comprises top and bottom platens 71 and 72, respectively, adapted to be mounted along the pressure lever and seal band, respectively, of a commercially available impulse sealer, such as one of the ALINE M-series impulse sealers, manufactured and sold by the ALINE Company of Santa Fe Springs, Calif. The specific embodiment depicted in FIG. 4a is a two-part heat sealing head adapted to be attached to an ALINE MC-15 Impulse heat sealer as an after market modification, and allows the MC-15 to produce pre-filled pouches of plasma for further processing in accordance with the system and method of the present invention.

The bottom platen 72 of the heat sealing head 70 is constructed of a suitable rigid, heat resistant material such as laminated Kevlar® manufactured and sold by the DuPont Corporation. In the illustrated embodiment, the bottom platen 72 is preferably about 15 inches in length in order to fit on the mounting surface of the MC-15 Impulse heat sealer. The bottom platen 72 includes a longitudinal slot 73 which is centrally disposed and runs along the entire length of the bottom platen 72. The width of the longitudinal slot 73 is approximately 0.2 inches in order to accommodate standard medical tubing, which typically has an outer diameter of approximately 0.1875 (3/16) inches, in nested fashion along the length of the slot.

A plurality of transverse slots 74 are provided at spaced-apart intervals along the length of the bottom platen 72 which are disposed in a direction orthogonal to that of the central slot 73. The transverse slots 74 have a width of approximately 0.5 inches and are located on 1.125 (1⅛) inch centers. Each transverse slot is, therefore, separated from its neighbors by a residual block of platen material centrally divided by the central longitudinal slot 73 which is about 0.625 (⅝) inches in width.

Both the longitudinal and transverse slots 73 and 74, respectively, are cut only partially through the material of the bottom platen 72, thereby forming a substantially flat bed 75 which defines the bottom surface of both the longitudinal and transverse slots. When the apparatus is used to form heat seals, a length of 0.1875 (3/16) standard medical tubing is nested in position along the longitudinal slot 73 and rests on the bed 75 of the bottom platen which functions as a bearing surface during the heat seal process.

A heating element 76, such as a nickel-chromium (NiCr) resistive wire, is provided in a snake-fashion from slot to slot and is disposed lengthwise along each transverse slot comprising the bottom platen in about the center of the slot. Where the heating element 76 traverses the center of the transverse slots 74, the NiCr wire is protected from contacting the thermo-sensitive plastic tubing by covering the wire with a piece of, for example, Teflon® tape. Blood or plasma samples contained in the pouches formed within the sealing device during the seal process are thus not damaged by the high temperatures of the heat seal.

The top platen 71 is also approximately 15 inches in length and is suspended over the bottom platen 72 by the pressure lever of the MC-15 heat sealer. The top platen 71 is constructed from a heat-resistant plastic material such as Lexan® or milled Kevlar® and comprises a set of equally spaced-apart, generally rectangular teeth protruding from its bottom, surface, and extending in a direction toward the bottom platen. The teeth 77 are about 0.5 inches in length and are spaced-apart on 1.125 (1⅛) inch centers. Accordingly, it can be seen that each of the teeth 77 is dimensioned to fit into the cavity defined by the transverse slots 74 of the bottom platen 72. Each of the teeth 72 of the top platen 71 is positioned to be suspended over a corresponding intersection of a transverse slot 74 and the longitudinal slot 73 of the bottom platen 72. Thus, each tooth 77 is configured to fit into the cavity thus defined when the heat seal platens are closed together by removal operation of the MC-15 device.

After a flexible tubing segment is placed within the longitudinal slot 73, the top platen 71 is pushed into contact with the bottom platen 72, by lowering the lid of the MC-15 heat seal apparatus. As the lid is lowered, the teeth 77 of the top platen 71 enter the cavity defined by the transverse slots 74 of the bottom platen 72 and contact that portion of the tubing segment which lies exposed on the bed 75 at the intersection of each transverse slot 74 with the central longitudinal slot 73. Current is provided to the nickel-chromium resistive heating wire which causes the plastic material of the tubing segment to soften. At the san time, the top platen 71 is compressed onto the bottom platen, thus applying pressure to the plastic material being softened by the heating element 76.

After sealing, the tubing segment is labeled on at least one end with a unique identifier that corresponds to the original plasma donation. This may be achieved by, for example, gluing a label onto the segment or by imprinting a bar coded emblem directly onto the tubing material. A prepared recess 78 is suitably provided on the heat sealer 70 for holding and aligning a pre-printed bar code identifier tag. Such a tag is formed from a suitable heat-sealable material and is heat sealed to the tubing segment at the first seal position for identification purposes. The tubing segment, including the sample containing pouches, is then frozen for preservation.

Returning to FIG. 2, it is important to be able to unambiguously identify all of the various parts of the system that comprise an individual plasma donation. Thus, unique identifiers such as coded threads, coded dots, bar codes, or other structure coded with the unique identifier, may be placed in the physical structure of the plasma collection system. For example, in one embodiment, a coded thread 37 is molded into the donation container 20, a coded thread 39 is molded along the edge of the bottle cap 22, a coded thread 41 is molded along the side of the test container 28, and a coded thread 43 is molded into the tubing segments at spaced-apart intervals. The unique identifier in the tubing segment runs along the length of the tubing segments and the code is repeated in order to permit segmentation of the tubing segments while maintaining identification integrity of each segment so prepared. Furthermore, each portion of the donation system is identified with the same code so that donation identity is maintained for all parts of the system.

Returning now to FIGS. 3a, 3b, and 4, it may be further desirable to have each individual pouch along a segment identified by an alpha or numeric code equal to the position of the pouch along the linear length of the original tubing segment. Such code may be imprinted, for example, on the compressed portion of the seal pad located between adjacent pouches by use of a stamping die. Such a stamping die may comprise an integral part of the sealing device as depicted in FIGS. 4 and 4a, so that sealing, forming pouches of variable sizes, and providing narrow or perforated areas for easy separation, as well as identification numbers, are all accomplished in a single efficient step. Alternatively, the alpha or numeric identifier could comprise part of a perforating jig or die.

Stamping dies are known which include means for advancing the alpha or numeric character to a next sequential one such that sequential pouches in a tubing segment are each identified by a corresponding sequential string of alpha (a, b, c . . . ) or numeric (1, 2,3, . . . ) characters.

Therefore, if a first testing pool is being prepared from pouches from several donations, a quality control check may be performed by confirming that all pouches to be pooled from each tubing segment have the same location code, for example, number 1. Likewise, when preparing a second testing pool from samples of the same donations, a quality control check may be performed by confirming that all pouches to be pooled from each tubing segment have, for example, the number 2 imprinted at some point on the compressed portion of the pouch.

In order to effect efficient PCR testing of a donation, the serology test sample taken from each individual donation in test container 28 is tested for various known antigens and/or antibodies which are designated for specific viruses. If a sample is positive for one or more known antigen or antibody tests, the individual donation and its corresponding tubing segment are excluded from further testing and both may be disposed of in an appropriate manner.

Tubing segments corresponding to the remaining serology negative donations are divided into identified groups, each group comprising a selected number of donations. As will be described further below, the number of donations per group is determined by the sensitivity of the specific high-sensitivity tests, such as a PCR test, the anticipated concentration of the viral RNA or DNA of interest in the plasma sample, and the anticipated frequency of a PCR positive sample occurring within the general donor population. For example, for the detection of the hepatitis C virus, containing the RNA of interest, in a population of repeat plasmapheresis donors, it is appropriate to pool samples of between 100 and 700 individual donations. For a population in which viral contamination occurs more often, smaller pools of between 50 and 100 individual donations may be appropriate.

One embodiment of a process of preparing a PCR testing pool in accordance with the present invention will now be described in connection with FIGS. 5 and 6. A sampling plate 80, generally similar in application to a titer plate but configured in accordance with practice of the invention, is provided. The sampling plate 80 is configured to contain generally hemi-cylindrical sample wells 81 disposed horizontally on the plate in a generally regular array. A suitable sampling plate used to practice the method of the invention has 64 such sample wells arranged in a 8×8, row/column, rectangular fashion. A cover plate 82 having approximately the same exterior dimensions as the sampling plate 80 is also provided. The cover plate 82 is adapted to cover the surface of the sampling plate 80 in close-fit attachment. Through-holes 83 are arranged on the cover plate in the same array fashion as the sample wells of the sampling plate 80. When the cover 82 is placed over the surface of the sampling plate 80, through-holes 83 line up vertically over the sample wells 81, thereby allowing communication with the sample wells through the through-holes. The diameter of the through-holes is substantially smaller than the surface area of the test sample pouches and the corresponding sample wells. However, the through-hole diameter is sufficiently large to permit a needle or other cannula like object to pass through the holes and enter the sample wells beneath.

As shown in connection with FIG. 6, a terminal (first generation, "number 1") pouch 84 is removed from each tubing segment that has been identified as belonging to a particular PCR group to be tested. Each terminal pouch 84 is washed, but not opened, and placed in a corresponding sample well 81 of the sampling plate 80. The cover plate 82 is secured over the top of the sampling plate 80 and the plate, cover, and pouches are thawed at an appropriate temperature.

An equal volume of between about 0.02 to 0.5 ml of plasma is removed from each pouch and pooled in a testing container. A needle 85 or other cannula like device is inserted through the through-hole in the cover plate and into the sampling plate sample well directly below, thereby piercing the tubing material of the side wall of the pouch and gaining access to the plasma sample therein. In an exemplary embodiment, the needle is connected to a device that provides a continuous vacuum or suction to extract all of the blood or plasma contained in the pouch and minimize any leakage of fluid into the surrounding tray. The needle may be held in a device which allows the needle to move through the through-hole and top wall of the pouch, but restricts its downward progress so that the needle is prevented from touching or piercing the bottom wall of the pouch as the pouch sits in the sample well. When the cannula is withdrawn after extracting a sample, the cover plate material 86 surrounding the through-hole prevents accidental withdrawal of the pouch along with the cannula, as depicted in FIG. 6.

While the method of preparing a PCR test pool has been described in terms of manually extracting a sample by inserting a cannula individually into each sample well, the method may equally be practiced using an automated process. The sampling plate containing pouches in each well may be held so as to allow an array of cannulas, arranged in a manner corresponding to the arrangement of through-holes in the cover plate, to be pressed down onto the sampling plate, thereby allowing all of die sample pouches to be pierced and samples extracted therefrom at the same time. Alternatively, a single cannula or cannula holding device may be automated or programmed to successively pierce and withdraw fluid from each pouch. In order to prevent carryover contamination, a clean cannula is used to withdraw samples for each pool.

In addition, it will be evident to one having skill in the art that the combination of sampling plate, sample wells, cover, through-holes, and cannula, while described in connection with extracting sample fluid from a sample packet, is equally applicable to extracting sample fluid from the Y-site sample containers of FIG. 2a. The configuration of the sample wells of FIGS. 5 and 6 are determined by the shape of the fluid-holding container, and only minor modifications are required to reconfigure them for Y-sites. For example, the sample wells may comprise an elongated cylinder, oriented vertically, into which each Y-site is inserted. A notch may be provided at some appropriate location about the upper periphery of each sample well which functions as a detent into which the Y-site's branch port may be positioned. This would also function to orient each Y-site and provide additional positional security. In the same manner as described in connection with FIGS. 5 and 6, fluid may be extracted from each Y-site by inserting a cannula through each Y-site's access port and into fluid communication with the sample. As the cannula is removed from the access port, the cover plate material surrounding each through-hole acts as a stop and prevents the Y-site from being withdrawn from the sample well.

It will be further evident to one having skill in the art that this configuration is equally suitable for practice of the invention using an automated process. An array of cannulas may be arranged in a manner corresponding to the arrangement of through-holes in the cover plate, thereby allowing all of the access ports of the Y-sites to be pierced and samples extracted therefrom at the same time. Alternatively, a single cannula or cannula holding device may be automated or programmed to successively pierce each access port and withdraw fluid from each Y-site.

An additional embodiment of an apparatus and method suitable for preparing a PCR testing pool in accordance with the present invention will now be described in connection with FIGS. 7, 8, 9a, 9b, and 10. Turning first to FIG. 7, a plasma donation pool comprising expressed fluids from a multiplicity of plasma samples is prepared from a number of plasma donation sample packets in an electrically powered hydraulic press 90. The hydraulic press 90 suitably comprises a crushing cylinder 91 in which sample packets are placed, and a hydraulically operated piston 92 which crushes the sample packets. The samples contained within the packets are expressed from the crushing cylinder 91 by a suitable compressed gas, such as compressed air or nitrogen, and collected in a pooling container as a pool.

Initially, a generational pouch (for example, pouch #1) is removed from each tubing segment that has been identified as belonging to a particular PCR group to be tested. Each generational pouch is washed, but not opened, and placed within the crushing cylinder 91 of the press 90. Loading of the crushing cylinder is performed within the environment of a class II biosafety hood and air-flow path so as to ensure against inadvertent contamination of the surrounding environment by a packet which has lost structural integrity. In a manner to be described in greater detail below, the crushing piston 92 is firmly seated into the open throat 91a of the crushing cylinder 91 in such a manner that containment of the contents of the crushing cylinder 91 is assured and that the cylinder 91 and piston 92 combination completely encloses the sample packets. The manner in which the crushing piston 92 engages the crushing cylinder 91 is designed to ensure that the environment outside of the cylinder 91 is protected from contamination by any harmful viruses that may be present in any of the samples contained by the sample packets.

The crushing cylinder 91 is next mounted on a cylinder seat 93 which aligns the cylinder in correct position on the hydraulic press 90 and further allows a hydraulic shaft 94, operatively connected to a hydraulic cylinder 95, to align with and mate to the crushing piston 92. In a manner that will be described in greater detail below, the crushing piston 92 is releasably connected to the hydraulic shaft 94, such that the piston 92 can be both raised and lowered by operation of the hydraulic cylinder 95.

After the cylinder 91 and piston 92 have been properly aligned on the cylinder seat 93 and connected to the hydraulic cylinder 95 through the shaft 94, a control valve 96 is operated so as to cause the hydraulic cylinder to exert a force on the shaft 94 and piston 92 which, in turn, crushes the sample packets within the crushing cylinder 91. The hydraulic cylinder 95 operates in conjunction with a four horsepower 240 volt AC electric motor 97 which operates a hydraulic reciprocating pump 98 which pumps hydraulic fluid in conjunction with a fluid reservoir 99 to thereby operate the cylinder 95. About 4,000 lbs of force is point loaded at the hydraulic shaft 94 which develops a pressure of about 800 to 900 psi applied to the sample packets by the piston 92.

After the sample packets have been crushed, the fluid donation samples contained therein are expressed from the crushing cylinder 91 by a compressed gas supplied by, for example, a compressed air cylinder 100 which is connected through a pressure regulator 101 to a pop-off valve 102 provided in the crushing piston 92. In order to allow the pop-off valve 102 to operate correctly, the piston 92 is first raised slightly from its fully extended crushing position. Compressed air is vented into the cylinder 91 through the pressure regulator 101 until the threshold pressure of the pop-off valve is reached. The valve 102 then opens, allowing the compressed gas to pressurize the interior of the cylinder which forces the plasma pool out of the crushing cylinder 91 through a collection port 103 provided in the bottom of the cylinder. The plasma pool is then collected in a pooling container connected to the collection port 103 by an express line or tube as the fluid is forced out of the cylinder by the compressed air. The compressed air is exhausted into a class II biological safety hood, after passage through a bleach trap.

Figure 8:
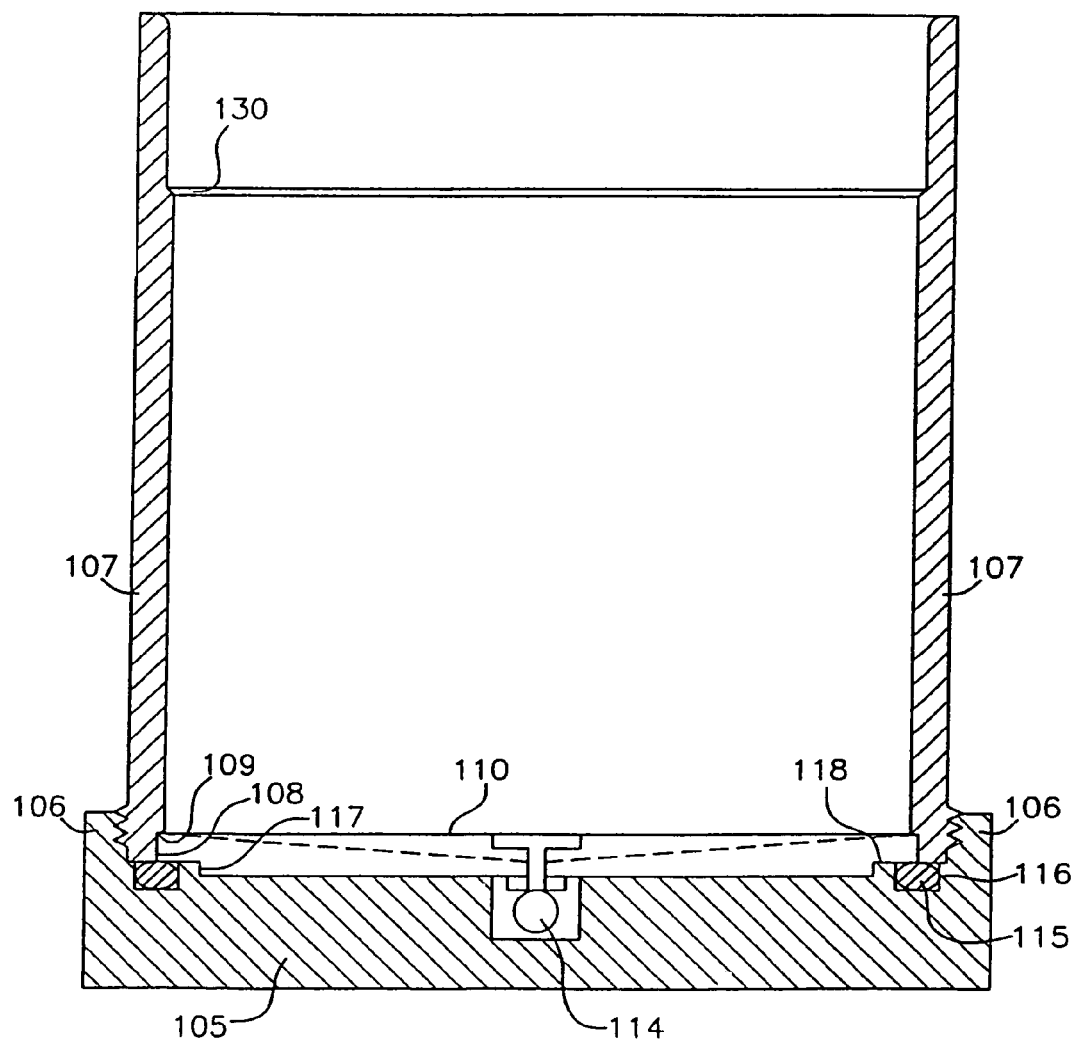
FIG. 8 is a semi-schematic cross-sectional view of a crushing cylinder of the device of FIG. 7.

Turning now to FIG. 8, there is depicted a cross-sectional, partially cut-away view of a crushing cylinder 91 constructed in accordance with principles of the invention. The crushing cylinder 91 suitably comprises a generally circular base plate 105 having a top and bottom surface and a circumferential lip 106 extending in an upwardly direction from the top surface, with threads cut into its interior face. A cylindrical cylinder wall 107, open at both ends, is threaded on the exterior face of its bottom end. A rabbet or notch 108 is cut into the interior face of the bottom end of the cylinder wall 107 so as to define an annular lip 109 which is disposed parallel to the top surface of the base plate 105 and presents an opposing face thereto. As the cylinder wall 107 is screwed into the base plate 105, a screen plate 110 disposed on the surface of the base plate 105 is engaged by the annular lip 109 of the cylinder wall 107 and compressed between the annular lip 109 and the top surface of the base plate.

Figure 9A:
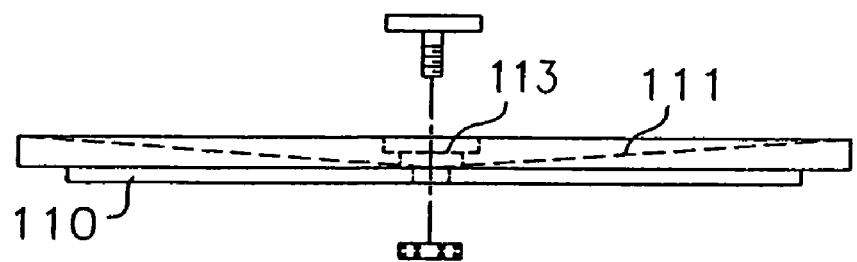
FIG. 9a is a semi-schematic partial cross-sectional view of a screen plate against which sample-containing packets are crushed.
Figure 9B:
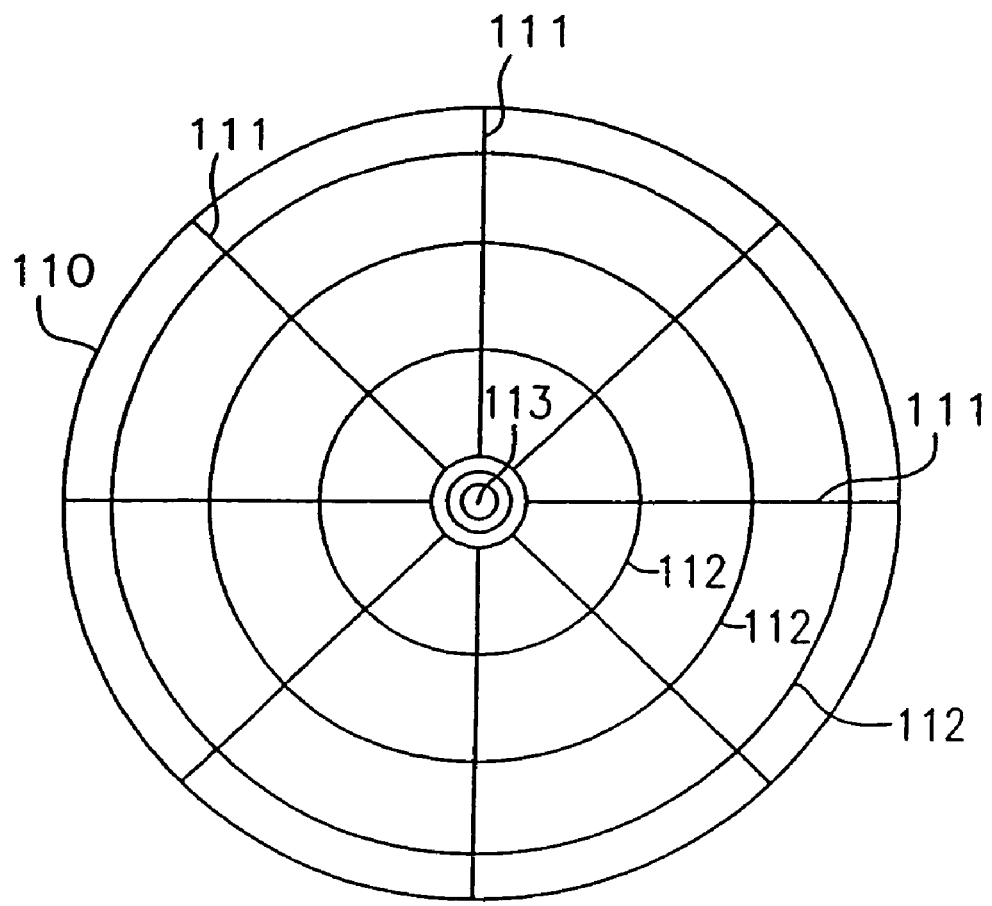
FIG. 9b is a semi-schematic top view of a screen plate showing radial and concenthc fluid gutters for collecting sample fluid from crushed sample containers.

Turning now to FIGS. 9a and 9b, the screen plate 110 is a generally circular, disc-shaped plate against which the sample containing packets are forced when they are crushed by the crushing piston 92. As is depicted in FIG. 9b, the screen plate 110 includes fluid gutters comprising radial slots 111 and concentric circular slots 112, all approximately $\frac{1}{32}$ inches in width, which are cut in the top surface of the screen plate. The radial slots 111 are cut at an angle which slopes toward the center of the screen plate 110 where they terminate into an axially located drain or sump 113 which drains through a $\frac{1}{4}$ inch drain pipe 114 (best seen in FIG. 8) drilled through the base plate 105.

Returning now to FIG. 8, a seal is formed between the cylinder wall 107 and the screen plate 110 by engaging and compressing an O-ring 115, provided in a seal race 116 cut into the base plate 105 for such purpose. The seal race 116 is located in the base plate such that the O-ring 115 lies beneath the vertical intersection of the screen plate 110 and the cylinder wall 107. A step 117 is cut into the base plate 105, and a mating groove 118 is cut into the screen plate, so that a positive detent is able to precisely locate the screen plate onto the base plate for proper alignment with the O-ring such that the cylinder wall 107 will properly engage the screen plate and their intersection will properly engage the O-ring 115.

Figure 10:
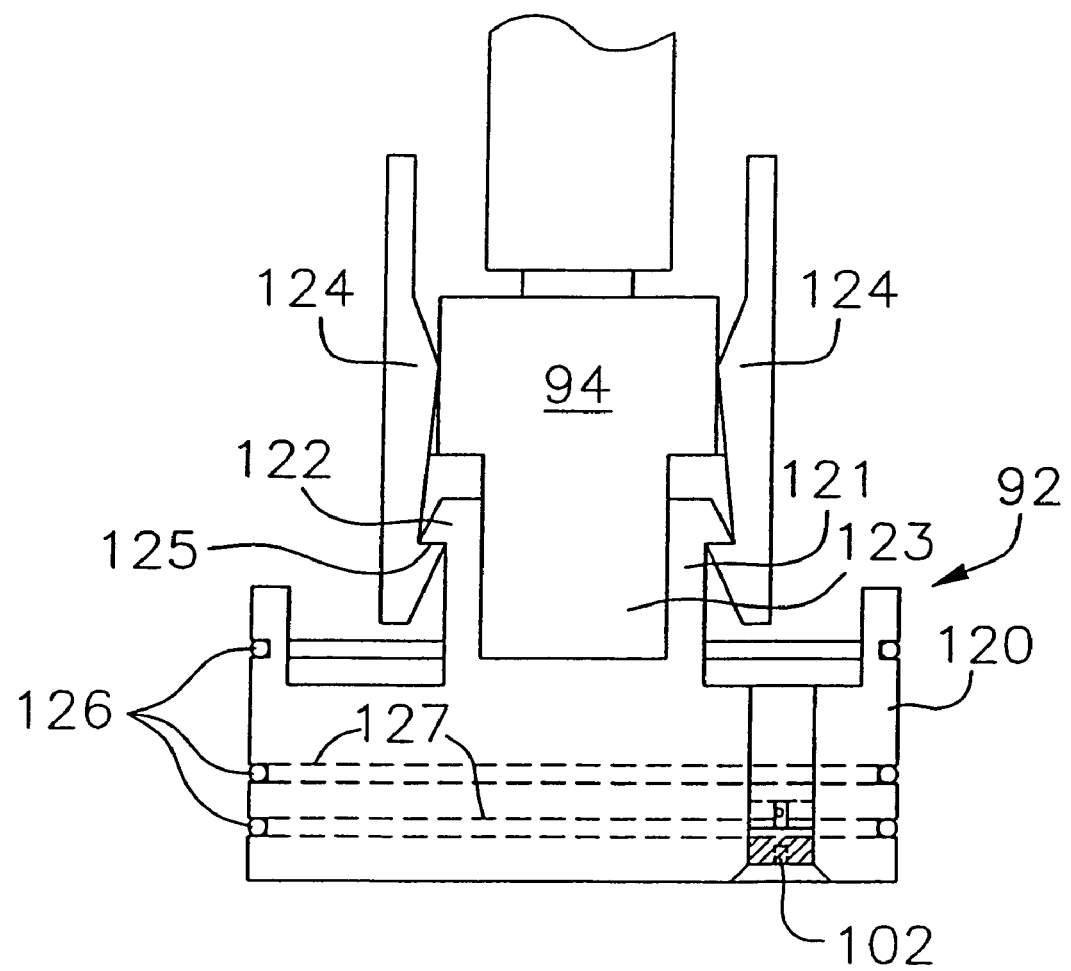
FIG. 10 is a semi-schematic partial cross-sectional view of a crushing piston of the device of FIG. 7.

Turning now to FIG. 10, there is depicted, in cross-sectional partial cut-away view a crushing piston 92 provided in accordance with principles of the invention. The crushing piston 92 comprises a generally cylindrical piston head 120, having an axially extending, centrally located cup 121 protruding therefrom, the cup 121 having generally cylindrical walls and one open end to define thereby a socket 123 for receiving a generally cylindrical hydraulic cylinder shaft 94.

An annular flange 122 is provided around the circumference of the cylindrical cup 121, and surrounds the cup's open mouth. The outer surface of the flange 122 is beveled, such that the beveled surface increases in diameter in the direction towards the bulk body of the piston head 120. As the hydraulic shaft 94 is advanced into the socket 123, a pair of spring-loaded retaining clips 124 are advanced over the beveled surface of the annular flange 122 until they detent into position and grip the underside of the annular flange.

To accommodate mating with the socket 123, each retaining clip 124 includes a beveled tooth 125 which rides along the beveled surface of the piston head's annular retaining ring 122, thereby spreading open the jaws of the spring loaded retaining clips 124. As the hydraulic shaft 94 continues to advance, the beveled teeth 125 of the retaining clips 124 are eventually advanced past the beveled surface of the annular retaining ring 122. The spring loading of the retaining clips forces the beveled teeth into contact with the outer surface of the cup side wall. The teeth of the retaining clips 124 are thus engaged with the underside surface of the annular retaining collar 122, thereby gripping the crushing piston 92 and providing means for causing the piston to move in both directions.

In addition, it will be evident to one having skill in the art that the spring loaded retaining clips 124 may be easily disengaged from the annular retaining ring 122 by a simple squeezing together of the ends of the clips opposite the beveled retaining teeth 125. Accordingly, it will be seen that the piston head 120, the cylindrical, axially mounted cup 121, the annular retaining ring 122 and the retaining clips 124, in combination, provide means for quickly and easily disconnecting the hydraulic shaft 94 from the crushing piston 92. This quick-disconnect feature allows the piston 92 and cylinder 91 combination to be easily removed from the cylinder seat 93 of the hydraulic pressure 110 for cleaning, sterilization, refilling with additional sample packets, and the like.

As is shown in FIG. 10, the crushing piston 92 further includes several O-rings 126 disposed in seal races 178 provided about the periphery of the piston head 120. The O-rings are provided in order to form a tight pressure seal between the exterior circumferential surface of the piston head 120 and the inner circumferential surface of the cylinder wall 107 of the crushing cylinder 91. Multiple O-ring seals provide a measure of safety and security, in order to ensure containment of potentially contaminated sample fluid within the confines of the cylinder 91. While three O-rings 126 are depicted in the illustrated embodiment of FIG. 10, it will be evident that a greater or lesser number of O-ring seals may be provided in accordance with the invention. All that is required is that a seal be formed between the crushing piston 92 and the crushing cylinder 91 so as to ensure containment of potentially contaminated fluid within the cylinder.

Returning now to FIG. 8, the crushing cylinder side wall includes a 0.020 inch beveled step 130 which is machined into the interior surface of the side wall. The first approximately 1.0 inches from the top, of the cylinder side wall 107 is thus, machined to have an inside diameter (ID) approximately 0.040 inches larger than the ID of the remaining portion of the cylinder side wall 107 which extends downwardly towards the screen plate 110 and base 105. The interface between the step and the remaining side wall portion is beveled, so as to provide a relatively smooth, angled transition from the slightly larger upper ID, to the slightly smaller lower ID.

The step on the cylinder side wall 107 is provided so that the crushing piston 92 may be manually inserted into the open throat of the crushing cylinder 91 with wily slight contact being made between the O-rings (126 of FIG. 10) and the ID surface of the cylinder. Once the manually assembled piston and cylinder combination is placed on the cylinder seat (93 of FIG. 7) the hydraulic shaft 94 is advanced to mate with the socket 123 of the piston and is extended until the retaining clips 124 detent against the underside surface of the piston head's annular retaining collar 122. The hydraulic shaft 94 is then further advanced so as to push the piston further into the cylinder, thereby pushing the O-rings beyond the step 130 on the ID of the cylinder wall. When pushed beyond the step, the O-rings fully compress between the ID of the cylinder side wall 107 and the piston seal races 127, forming thereby a tight seal.

In operation, the crushing piston 92 develops pressure of about 800 to 900 psi (4,000 lbs of force point loaded at the hydraulic shaft) which is a sufficient pressure to crush the sample packets contained within the cylinder. Blood or plasma sample fluid flows along the fluid gutter provided in the screen plate and into the central sump, where it is collected and allowed to flow out the extraction port and into a pooling container. Following the crushing operation, the hydraulic cylinder 95 is operated to raise the crushing piston 92 a small distance (approximately ½ to 1 inches) above the mass of crushed sample packets, thereby creating a chamber within the cylinder. A pressurized gas, such as compressed air, is forced into the chamber through the pop-off valve 102 in the piston 92. Pressurizing the chamber causes any remaining blood or plasma sample fluid to be expressed out of the cylinder through the outlet port 103 into the pooling container.

Once the crushing and pooling operation is completed, the express line connected to the outlet port 103, is clamped, to prevent any additional sample fluid from exiting the cylinder. The express line is placed into a bleach container, and the hydraulic cylinder 95 is caused to raise the piston further in the cylinder, thereby creating a suction which siphons bleach from the container into the cylinder. Preferably, the crushing and bleach siphoning steps are repeated two additional times, in order to ensure that any blood or plasma sample "flash back" fluid is fully expressed from the crushing cylinder 91 and that the bleach has ample opportunity to fill the interior volume of the crushing chamber, thereby reducing any gross viral contamination that may be found within.

Next, the quick release clamps are operated and the piston/cylinder combination is removed from the hydraulic press 90 and subjected to sterilization procedures in, for example, an autoclave. The piston and cylinder may be subsequently chemically cleaned by soaking them in a 10% bleach solution for fifteen minutes, followed by a rinse cycle of $H_2O$, 1% SDS (sodium dodecyl sulfate) surfactant, and $H_2O$ again, prior to autoclaving. If there is insufficient time for autoclave sterilization, the chemical clean may be concluded with a 70% ETOH and sterile $H_2O$ solution. If such additional chemical cleaning is desired, it is performed in a class II biosafety hood which exhausts through a HEPA filter. While under the hood, the crushing cylinder is loaded with a next group of sample packets to be crushed and the crushing piston 92 is manually inserted into the open mouth of the crushing cylinder 91 and forced down until the pistons O-rings make contact with the beveled step formed in the side wall of the cylinder. The newly reloaded cylinder/piston combination is now ready to be placed on the cylinder seat 93 of the crusher 90. The hydraulic cylinder 95 is operated to cause the hydraulic shaft 94 to lower onto the piston 92 such that the quick release clamps engage the annular retaining ring on the piston. The crushing, expressing, and bleach-cleaning process is now repeated.

From the foregoing, it will be evident to one having skill in the art that the electrically operated hydraulic press (the crusher) 90 allows harvesting of blood or plasma samples from a great number of sample packets in a minimal amount of time. The number of sample packets able to be crushed by such an apparatus is limited primarily by the scale of the device and the pressure able to be developed by the crushing piston against the mass of sample packets contained in the cylinder. The 800 to 900 psi of pressure developed by the hydraulic press of the illustrated embodiment is sufficient to completely crush up to 64 sample containing packets of the type described in connection with FIG. 2. Accordingly, large scale pools comprising up to 512 samples, can be formed by 8 operation cycles of the crusher of the present invention. This would provide a significant reduction in pool formation time over a method in which 512 sample packets were individually accessed by a cannula to harvest the samples therefrom.

In addition, it will be apparent to one having skill in the art that a single large scale pool, comprising up to 512 samples or more, can be formed from a crusher apparatus made sufficiently large enough to accommodate the greater number of sample pockets in the cylinder. The hydraulic press portion would also be increased in size to provide greater crushing power to overcome the greater resistance of the increased number of pockets. As was mentioned above, the pool size would only be limited by the desired scale of the crusher.

Figure 11:
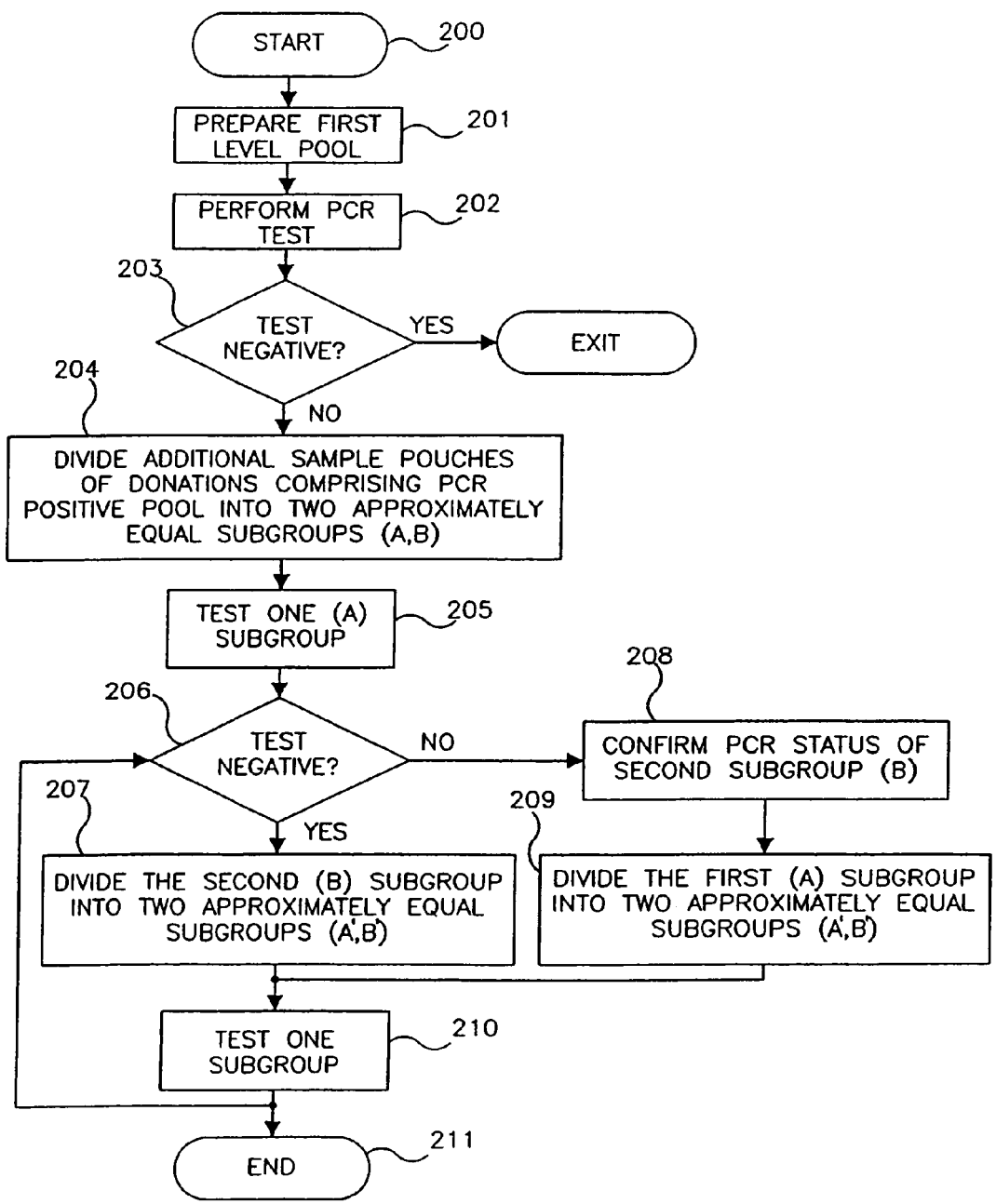
FIG. 11 is a flow chart depicting the test methodology according to the invention for determining PCR positive donors from a donation pool.

Referring now to FIG. 11 there is shown a flow chart of a PCR test methodology according to the invention, which allows for the identification of a unique PCR positive donation with the fewest number of individual tests.

The process begins at block 200 with the definition of an appropriate initial pool size which, in turn, depends on various factors such as the frequency of occurrence of the virus of interest in the general donor population, the likely final concentration of viral DNA or RNA after dilution in the pool, and the like.

Although the PCR test is highly sensitive and is capable of detecting a single virus in a contaminated sample, a virus must necessarily be present in the sample for the PCR test to provide a positive result. If, for example, a sample from a contaminated donation having a relatively low virus concentration is pooled together with a large number of uncontaminated samples, the concentration of virus in the resulting pool may be so low that there is a statistical probability that no virus is present in a sample taken from the pool for PCR testing. Such pools may, indeed, falsely test negative for viral contamination.

For example, if a 0.02 ml sample was prepared from a plasma donation contaminated with viruses at a concentration of 500 viruses per mll of sample, the 0.02 ml sample would comprise, on average, 10 viruses. If this 0.02 ml contaminated sample were pooled with approximately 500 other 0.02 ml samples from uncontaminated donations, the resulting 10 ml pool would comprises viruses at a concentration of 1 per ml. Accordingly, if a 1 ml sample were taken from the pool for PCR testing, there is a significant statistical probability that the PCR sample will contain no viruses.

Such low concentrations of virus contamination pose little threat for products produced from plasma, because several methods are available for inactivating viruses present in such low concentration donations. Such viral inactivation methods include the use of solvent/detergent or heating at over 60° C. for an appropriate time or the like. These methods, generally, are described as being capable of reducing the concentration of viruses by a number of "log units." For example, the solvent detergent method is capable of reducing the viral contamination of hepatitis C by at least $10^7$ per ml or "7 log units." Thus, plasma products such as factor VIII, factor IX or prothrombin complex may be prepared from plasma donations routinely treated by, for example, the solvent detergent method after having been PCR tested negative.

For blood products, routinely transfused directly to a recipient, there remains some small risk of low concentration viral contamination, after such donations have PCR tested negative.

In the embodiment illustrated in connection with FIG. 11, the factors discussed above, such as the frequency of occurrence of the virus of interest in the donor population and the likely concentration of the virus alter dilution, are evaluated. An appropriately sized first level PCR testing pool is designed which minimizes the statistical probability that viruses present in low concentrations will go undetected. The pool is prepared at block 201 by pooling the contents of terminal pouches of identified tubing sections, in the manner described above. At block 202, a PCR test is performed on the first level PCR pool.

Block 203 represents a decision point in the methodology of the invention which depends on the results of the PCR test performed in block 202. In the event of a negative result on the test, all of the donations corresponding to samples used to make up the first level PCR pool are presumed to be free of viral contamination and released for further processing into pharmaceutical products. The methodology thus exits on receipt of a negative PCR test result. When the PCR test returns a positive indication, this indicates that a viral contaminant is present in one, or more than one, of the donations which made up the original PCR first level pool. At block 204, an additional sample pouch, the pouch next to the one first removed, is taken from tubing segments which correspond to donations comprising the original PCR first level pool. These additional sample pouches are divided into two approximately equal subgroups, designated A and B herein for purposes of clarity.

These subgroups are then separately pooled using a separate, clean cannula to form each subgroup pool in the same manner as described above, and only one of the subgroup pool is PCR tested, as indicated at block 205. It is immaterial for purposes of the invention which of the two subgroups is tested. In block 205, subgroup A is identified as the subgroup to be tested, but subgroup B could just as easily have been designated without disturbing the methodology of the invention.

At block 206, a decision is made depending on the outcome of the PCR test of subgroup pool A. In the event that subgroup pool A tests negative for a PCR viral indication, no further testing is performed on samples from donations that comprised subgroup A. Rather, as indicated at block 207, the next sample pouches in sequence are taken from tubing segments that comprised subgroup B which are then, in turn, divided into two approximately equal subgroups A' and B'. Each subgroup in this step comprises approximately half the number of samples as comprised the immediately preceding subgroup. The contents of the subgroup sample pouches are again pooled separately in the same manner as described above. In the event that subgroup A tested PCR positive, indicating at least one of its component donations was virus contaminated, the other untested subgroup (subgroup B in the example of FIG. 11) is now PCR tested at block 108 to confirm that it is not also PCR positive. Subgroup A now becomes the subgroup further subdivided into two approximately equal subgroups (A' and B'), as indicated at block 209.

At block 210, PCR testing is performed on only one of the subgroup pools, A' or B', defined in preceding step 207 or 209. The method now iterates and returns to block 206, wherein the decision step is applied to the results of the PCR test performed at block 210. Again, if the PCR test results prove negative for the tested subgroup, the untested subgroup would be further subdivided into two approximately equal subgroups, each comprising approximately half the samples of the preceding subgroup. If the tested subgroup returned a PCR positive result, the tested subgroup would be further subdivided into two approximately equal subgroups, each of which would comprise one half of the samples of the preceding subgroup. In this case, the untested subgroup would again be PCR tested in order to confirm that it was not also PCR positive.

The test methodology continues iterating from block 206 through block 210 until testing is determined to be complete. Test completion is defined as when a subgroup division results in the creation of two subgroups, each containing only one sample pouch corresponding to a single donation. One of the samples is PCR tested at block 210 and, if the test results are negative, the other sample is identified as belonging to a virally contaminated plasma donation. If the tested sample tests positive, the remaining sample is then also PCR tested in order to confirm that it is not also PCR positive.

Upon completion of all testing, the methodology of the invention ends at block 211. It should be clear from the flow chart of FIG. 11, that the testing methodology of the invention only requires that two PCR tests be performed at each test level when the initially tested pool is positive: One initial test for one of the two subgroups, and one subsequent test to confirm that the corresponding initially untested pool is indeed negative. The test methodology requires only a single PCR test at each test level when the initially tested pool is negative.

Figure 12:
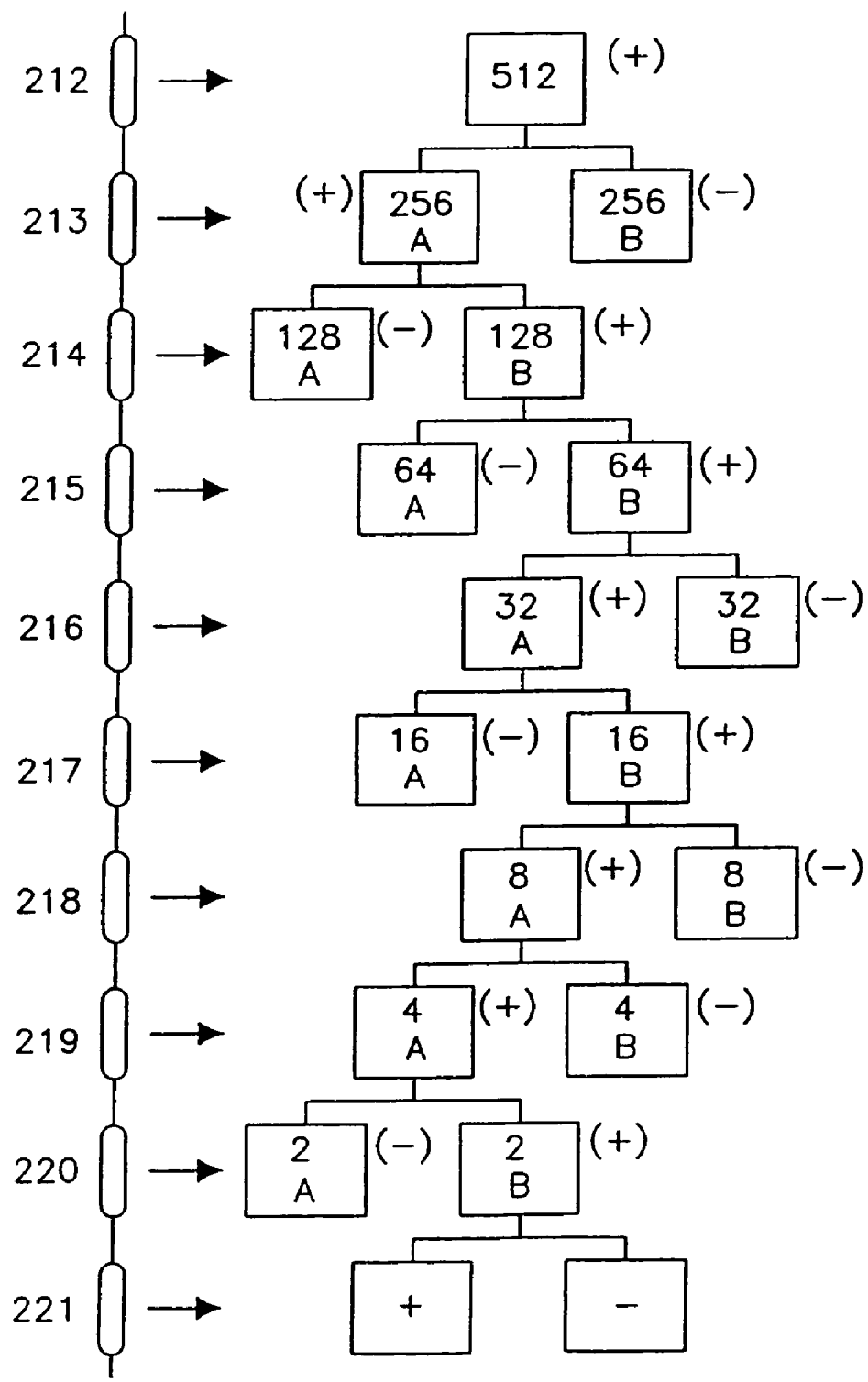
FIG. 12 is a flow chart depicting a test sequence according to the invention for identifying a single PCR positive donation from a 512 donation pool.

Application of the system and method for sample testing of the invention will now be described in connection with a particular PCR test pool size, as depicted in FIG. 12. In FIG. 12, the terminal pouches of 512 individual donations are formed into an initial PCR testing pool at 212. For purposes of illustration, it will be assumed that only one of the 512 samples was taken from a donation which was contaminated by a virus of interest. The tubing segment depicted in FIG. 12 which comprises 10 individual and connected pouches represents the tubing segments originally connected to and taken from the contaminated plasma donation container.

The initial 512 sample pool is PCR tested and because of the presence of the contaminated sample, returns a positive viral indication. At step 213, two 256 donation pools (256A and 256B) are prepared from the next sequential pouches taken from segments that made up the prior positive pool. Pool 256B is now PCR tested and, as depicted in FIG. 12, returns a negative viral indication, thus indicating that pool 256A contains a sample from the contaminated donation.

At step 214, two 128 donation pools are prepared from the next sequential pouches of tubing segments that made up pool 256A. Thus, according to the invention, pool 256A has been subdivided without having been PCR tested. At step 203, pool 128A is now PCR tested and, since it returns a negative viral indication, pool 128B is now known to include a sample pouch from the contaminated donation. Pool 128B is then subdivided into two 64 donation pools (64A and 64B) by removing the next sequential pouch from those tubing segments whose preceding pouches made up pool 128B.

Next, pool 64B is PCR tested and, in the example of FIG. 12, returns a positive viral indication. In this case, PCR testing is performed on pool 64A in order to verify that it is, indeed, negative and that no additional contaminated samples are present beyond those in pool 64B. At step 216, pool 64B is further subdivided into two 32 donation pools, 32A and 32B, by removing the next sequential pouch from tubing segments used to make up preceding pool 64B. Pool 32B is PCR tested, returns a negative viral indication, as indicated, and pool 32A is therefore further subdivided into two 16 donation pools, 16A and 16B. Again, the 16 donation pools are prepared by removing the next sequential sample pouch from tubing segments that made up the preceding positive pool, 32A.

At step 217, pool 16B is PCR tested and returns a positive viral indication. Pool 16A, therefore, is PCR tested in order to confirm that it is negative, and that all contaminated samples are present in pool 16B.

At 218, pool 16B is subdivided into two 8 donation pools, 8A and 8B, by removing the next sequential sample pouch from tubing segments that made up the preceding positive pool 16B. Pool 8B is then PCR tested and, as illustrated, returns a negative viral indication, indicating that pool 8A contains a sample from a contaminated donation. Pool 8A is then further subdivided into two 4 donation pools, 4A and 4B, at step 219. PCR testing is performed on pool 4B, which returns a negative indication, thus indicating that pool 4A contains a sample from a contaminated donation. Pool 4A is then subdivided, at 220, into pools 2A and 2B in the same manner, as described above. Upon PCR testing, pool 2A returns a negative viral indication indicating that one of the two samples comprising group 2B was taken from a tubing segment of a corresponding contaminated donation.

At step 221, the individual donations are tested by removing the final pouch from the tubing segments that made up group 2B. The final individual donations are PCR tested in order to identify the specific positive donation, which is then removed from storage and appropriately disposed of. The remaining 511 viral free donations are retained for further processing into pharmaceutical products.

In the above example, a single contaminated donation has been uniquely identified from a group of 512 such donations, by performing only 13 separate PCR tests, including the primary PCR test on the original 512 donation pool. The method of the invention, allows for skipping a PCR test on a particular subpool, so long as the corresponding tested subpool returns a negative viral indication. By thus skipping certain PCR tests, the method of the invention reduces the number of PCR tests that must be performed in order to identify a specific positive donation, without sacrificing the resolution of the PCR test methodology. Under the method of the invention, all positive donations will be identified but without requiring that all donations be tested.

From the exemplary embodiment of FIG. 12, it will be clear that either one of the successively smaller subgroups may be PCR tested and that the arbitrary position of the positive sample may be varied. Thus, if a sample from the positive donation were present in each initially tested subpool, 18 tests would be required to uniquely identify the positive donation (one initial test which returns a positive indication and one additional test to assure that the corresponding subpool is negative).

By the same token, if each initially tested subpool returns a negative indication, 10 tests would be required to identify the positive donation. In practice, positive and negative test results on the subpools would tend to distribute equally, thus, 14 tests on average would be required to identify a uniquely positive donation from an initial donation pool for 512 units.

It is therefore clear from the foregoing that the system and method of the present invention, including the provision of tubing segments comprising individual and connected pouches each containing a sample of a plasma donation, is advantageous in providing a multiplicity of PCR test pools. Unlike conventional pool preparation, in which a sequence of initial and subsequent pools are formed from a single sample of each donation at the same time, the present invention allows for formation of a test pool immediately prior to testing. This manner of "just-in-time" pool formation permits construction of test pools from individual pouches only as needed. The possibility of contamination is eliminated since the pools are constructed at different times, each from sealed sample pouches. Moreover, sample pouches remain frozen until needed to develop a test pool. Multiple freeze-thaw cycles which may adversely affect the recovery of the DNA or RNA of interest are avoided, thus insuring the integrity of the PCR test.

While the above-described method is effective for identifying a viral positive donation with the fewest number of relatively expensive PCR tests, other methods for identifying individual positive donations are also provided in accordance with practice of the present invention. In particular, one such method has the property of being able to identify individual positive donations within two to three PCR testing cycles, thus significantly reducing the amount of time and administrative overhead required to screen a large number of donations.

For example, in the above-described method, once a particular subpool has been identified as containing a positive donation, a technician must identify those donations which contributed samples to form that particular subpool. Those donations must then be revisited, and an additional sample packet must be harvested from each corresponding tubing segment. Two next-generation subpools must then be formed, and PCR testing repeated. This harvesting, subgroup pool formation, and PCR testing process is repeated for smaller and smaller generational subpools until the method uniquely identifies the virally contaminated donation.

However, a significant amount of time is consumed in each PCR testing cycle (harvesting, subgroup pool formation, and PCR testing). Talking the 512 sample first generational pool as an exemplar, it will be evident that at least 10 PCR testing cycles will be required to identify a unique viral contaminated donation. While highly cost-effective, the above-described method may present challenges to a PCR testing laboratory when time is of the essence.

A methodology for uniquely identifying viral positive blood or plasma donations in the fewest number of PCR testing cycles will now be described in connection with FIGS. 13 and 14.

Figure 13:
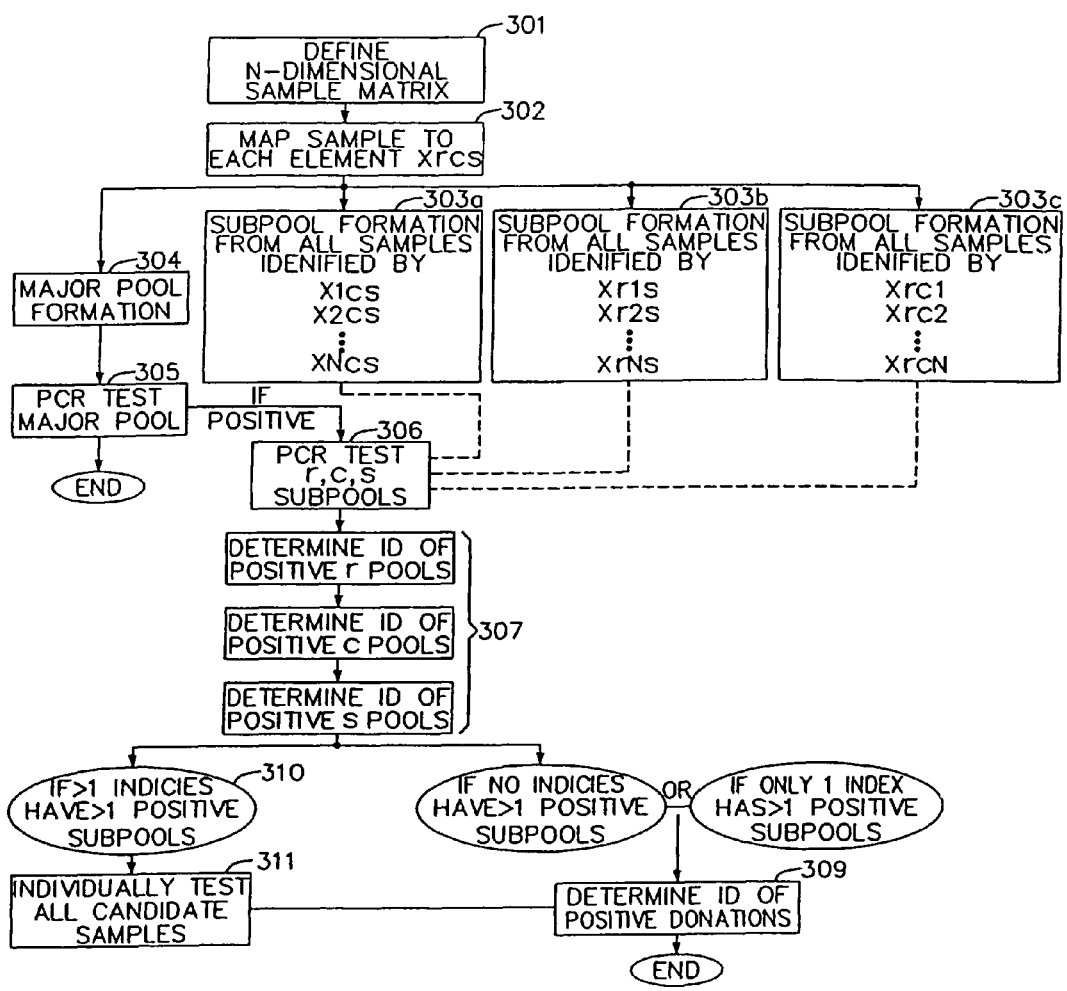
FIG. 13 is a flow chart depicting a second test methodology according to the invention for determining PCR positive donors from a donation pool.

Turning now to FIG. 13, there is depicted a flow chart of a PCR testing methodology, in accordance with the invention, for efficiently detecting a PCR positive individual donation in a pool with the minimum number of PCR analysis cycles. As was the case with the prior-described PCR testing method, the method of FIG. 13 assumes that the PCR test has sufficient sensitivity to detect the presence of a positive sample in a pool of the appropriate size. For purposes of illustration only, the initial grouping has been chosen to represent 512 blood or plasma donations. It will be understood by those having ordinary skill in the art that the initial grouping size may be larger or smaller depending on the particular genome marker being evaluated, the sensitivity of the PCR test procedure used, the expectation value of the genome marker concentration within a sample aliquot, and the sample aliquot size.

The method begins in block 301 by defining an N-dimensional sample matrix or grid. The matrix may be of any size and comprise any number of dimensions from 2 to N, but preferably is a 3-dimensional regular matrix, organized as a square.

Figure 14:
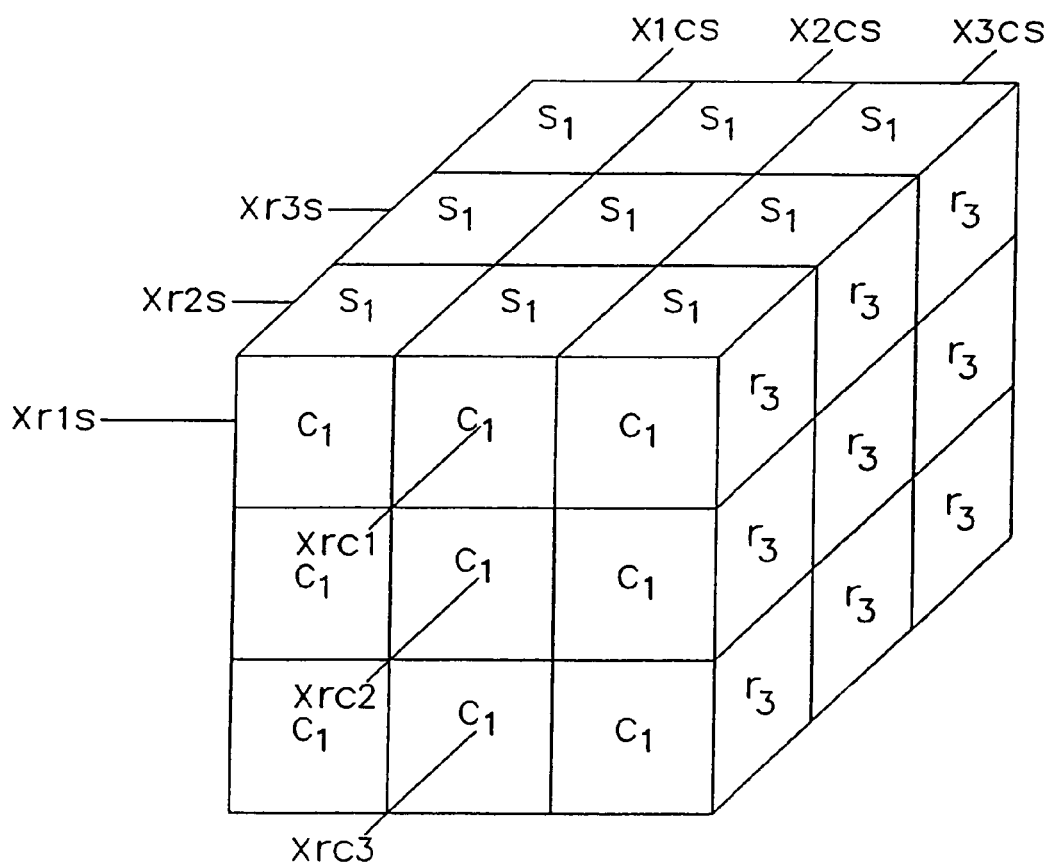
FIG. 14 is a representation of a 3-dimensional grid according to the invention showing the definition of r, c, and s indices.

An example of such a matrix is depicted in FIG. 14, which is a graphical illustration of square matrix, characterized by 3-dimensional; row, column, and slice (r,c,s). In the exemplary matrix of FIG. 14, there are 3 rows, 3 columns, and 3 slices, thereby defining $3^3$, or 27, elements. In the exemplary embodiment, a row is considered as comprising all of the elements defined by taking an imaginary vertical section through the square regular matrix. In the embodiment of FIG. 14, the elements comprising, for example, row 3 of the matrix are identified by the letter $r_3$ on their row faces.

Likewise, a column comprises all of the matrix elements defined by taking a second imaginary vertical section through the matrix, in a direction orthogonal to the direction of a row. In the exemplary embodiment of FIG. 14, the elements that comprise, for example, column 1 have the letter $c_1$ on their column faces. A slice is defined as all elements comprising a horizontal section taken through the exemplary matrix of FIG. 14. In like manner to the row, column, definition, the elements comprising slice 1 are identified with the letter $s_1$ on their slice faces.

It can be seen, therefore, that each of the 27 elements in the matrix of FIG. 14 uniquely belongs to 1 of the 3 rows, 1 of the 3 columns, and 1 of the 3 slices. Mathematically, this may be expressed by the relationship $X_{rcs}$, where X denotes an element, and rcs is a dimensional index, where each of the indices may take on a value from 1 to 3. The specific element $X_{113}$ may be identified as that element at the intersection of row 1, column 1, and slice 3.

From the foregoing, it will be apparent that although the exemplary matrix of FIG. 14 is a 3×3×3 matrix, the principles of matrix definition and element formation will hold for matrices with a much greater number of rows, columns, and slices. In particular, an 8 row, 8 column, 8 slice matrix may still be represented mathematically as $X_{rcs}$, where rc and s may now take on values from 1 to 8. Thus, a 3-dimensional 8×8×8 matrix is able to accommodate identifiers for 512 elements.

Returning now to the method flow diagram of FIG. 13, following definition of an N-dimensional sample matrix, particular blood or plasma donation samples are mapped to each of the elements defined by the matrix. In an exemplary 3-dimensional 8×8×8 matrix, a sample from each of 512 individual donations is associated with a matrix element, and identified by a corresponding, unique $X_{rcs}$ indicator.

Next, an aliquot is taken from each sample, and a multiplicity of minor sub-group pools are formed. Each minor pool comprises the aliquots of all of the samples ($X_{rcs}$) in which 1 of the dimensional indices is fixed. In other words, in accordance with the above-described exemplary matrix, all of the samples ($X_{rcs}$) which have r=1, regardless of the column or slice value, are formed into a minor pool; likewise for r=2, r=3 ... r=N; likewise for c=1, regardless of row or slice value, c=2, ... c=N; likewise for s=1, regardless of row or column value, s=2 ... s=N. Each minor pool thus represents each row, column, layer, or other dimensional index, such that if an N-dimensional matrix has been defined, there will be N-dimensions times the (total number of samples)$^{1/n}$ minor pools. For the exemplary 3-dimensional 8×8×8 matrix containing 512 samples, there will be 24 minor subgroup pools (8 row pools, 8 column pools, and 8 layer pools). The creation of minor pools, in accordance with the invention, may be viewed as being similar to the mathematical method of reducing a determinant by the method of minors. In like manner, each sample will be understood to be represented in N minor pools, 1 for each dimension of the matrix.

In addition to forming the minor pools, an aliquot of each sample, or an aliquot of each of the minor pools, is combined to form a single master pool which contains a sample from all of the 512 donations comprising the present donation space. After all of the pools are formed, any remaining samples and the minor pools and master pool may be refrozen and stored until such time as PCR testing is desired.

When PCR testing is desired, a PCR test is first performed on the master pool which represents an aliquot of each sample comprising the matrix. If the test results for the master pool are negative, there are, at least to the sensitivity level of the PCR test, no viral positive donations represented by samples forming the matrix. The blood or plasma donations which have contributed samples to the matrix may be released for further use. However, if the PCR test of the master pool is positive for a particular genome marker, a second PCR testing cycle is entered, at 300, in which each of the minor pools are now tested.

In a manner similar to that described above, the major pool sizes chosen such that the statistical probability of their being more than one positive sample in the major pool (the 512 samples) is small, preferable less than 1 to 2%. This can be done by evaluating the frequency of occurrence of the virus of interest in the general donor population to a 98% to 99% confidence level. For example, if it is determined that only 1 donor out of a general donor population of 1,000 is contaminated with the virus of interest to a 98% confidence level, there is a 2% probability of finding more than 1 contaminated donor in the next 1,000 donors being evaluated. This assures that the algorithm will, in general, be able to identify the single reactive unit in a pool of appropriate size within the PCR testing cycle. In accordance with the invention, given a single positive sample within the matrix, 3 of the minor pools will contain an aliquot of the positive donation, 1 in each dimension. In the exemplary embodiment (the matrix of 512 samples), there are 8 minor row pools, 8 minor column pools, and 8 minor layer pools. If the master pool tests positive, then 1 row, 1 column, and 1 layer pool will test positive during the second PCR testing cycle as shown at 307. The intersection of the row, column, and layer element index unambiguously identifies the reactive donation as shown at 309.

As an example, if the reactive sample has been mapped to matrix element $X_{113}$ the row 1 minor pool will return a positive PCR test result, while the row 2, and subsequent row minor pools will test negative. Further, the column 1 minor pool will return a positive test result, while the column 2 and subsequent column pools will test negative. Likewise, the layer 1 and 2 minor pools will return a negative result, the layer 3 pool will test positive, and subsequent layer minor pools will test negative. The 3 positive minor pools (row 1, column 1, and layer 3) have only a single element in common, $X_{113}$. Thus, the positive donation is uniquely identified as represented by the sample mapped to element $X_{113}$.

If there is more than 1 reactive donation in the matrix, the reactive donations may still be unambiguously identified by the method of the invention, by no more than 1 additional PCR testing cycle. If it is observed that more than 1 minor pool of a single dimensional index returns a positive test result, while only a single minor pool representing each of the remaining dimensional indices returns a positive test result, the more than 1 positive donations may be unambiguously identified by mathematically evaluating the test results without the need for a third PCR testing cycle.

For example, if a row 1 minor pool, and none other, tests positive; a column 1 minor pool, and no other, tests positive; and a layer 1 minor pool and layer 3 minor pool both test positive, there are only two positive donations comprising the matrix, and they are able to be unambiguously identified as $X_{111}$ and $X_{113}$. No further testing is required to arrive at this result.

If, on the other hand, it is observed that multiple minor pools test positive and their identities indicate changes along 2 dimensional indices as shown at 310, it will be apparent that there will be $z^2$ elements identified as potentially mapped to a positive donation, where z is the actual number of positive donations comprising the grid.

For example, if the row 1 minor pool, and no other, tests positive; the column 1 and column 3 minor pools test positive; and the layer 1 and layer 3 minor pools test positive, this suggests that the potentially positive candidate elements are $X_{111}$, $X_{113}$, $X_{131}$, and $X_{133}$. Since there is a multiple in only two of the dimensional indices (column and layer), and for candidate elements, it will be seen that there are only two actual positive donations comprising the matrix. In this circumstance, all 4 donations may be arbitrarily identified as being positive, and disposed of or, alternatively, an aliquot may be taken from each of the 4 candidate elements and individually PCR tested during a third PCR testing cycle at 311, in order to uniquely identify which 2 of the 4 comprise the actual positive donations.

In like manner, it is mathematically evident that if there are more than 2 positive donations in the matrix, and their identifiers vary in more than 2 dimensions, there will be, at most $z^n$ potentially positive candidate elements identified, where z is the actual number of positive donations, and where n is the number of dimensions which vary. In this circumstance, aliquots are taken of all suspect elements in the matrix and directly tested.

Thus, it can be seen that the method of the invention permits unambiguous identification of donations which are reactive for a particular genome marker within a single PCR testing cycle for an initially positive master pool, within 2 PCR testing cycles for all matrices which contain a single reactive donation or a multiplicity of reactive donations which vary along only a single dimensional index, and within 3 PCR testing cycles for any other situation.

Accordingly, the practice of the present invention results in the blood supply, and blood or plasma products prepared therefrom, being substantially safer by virtue of its being as free as possible from viral contamination. Advantageously, cost-effective, high-sensitivity testing is readily performed for the presence of a virus directly. Thus, false indications of virus contamination usually associated with antibody testing during the infectivity window period is avoided. Moreover, the present invention allows cost-effective use high-sensitivity tests which are capable of detecting the presence of a single virus in the test sample, thus helping to insure the freedom of the blood supply from incipient viral contamination.

Those skilled in the art will appreciate that the foregoing examples and descriptions of various preferred embodiments of the present invention are merely illustrative of the invention as a whole, and that variations in the shape, size, and number of the various components of the present invention, as well as the types of tests implemented, may be made within the spirit and scope of the invention. For example, it will be clear to one skilled in the art that the length of the individual and connected pouches, and therefore their volumetric content, may be progressively increased along the length of the tubing segment. As successive testing subpools are formed from a smaller and smaller number of samples, the volume of plasma comprising the pool necessarily decreases. It should be clear that in order to maintain a sufficient volume of plasma in each successive subpool, successive sample pouches may contain a larger volume in order to accommodate a desired final pool volume. In order to accommodate pools ranging in size from about 1 ml to about 10 ml, it will be clear that the volumes of successive sample pouches will increase from about 0.02 ml to about 0.5 ml, in progressive steps. In one exemplary embodiment, the pouch volume is 0.02 ml the first pouch to be used in the largest pool and is 0.2 ml in the final pouch.

It will also be clear to those skilled in the art that the system of the invention is not limited to the exemplary plasma collection container and an associated tubing segment. Blood bags or other biological fluid containers may be used with equal facility and suitable tubing segments may be attached thereto both prior to fluid collection and after fluid collection is completed. All that is required is that sample quantities of biological fluids be transferred to a tubing segment which is then formed into pouches in accordance with practice of the invention.

Accordingly, the present invention is not limited to the specific embodiments described herein but, rather, is defined by the scope of the appended claims.

What is claimed is:

1. A method for identifying viral positive biological fluid donations in the fewest number of high-sensitivity test cycles, the method comprising:
   (a) providing a multiplicity of biological fluid donations;
   (b) taking a single aliquot from each of the multiplicity of fluid donations and combining said aliquots into a single master pool;
   (c) testing the master pool for viral indication using a high-sensitivity PCR test;
   (d) providing an indication to a user as to whether the master pool contains a viral positive sample;
   (e) where the master pool is found to contain a viral positive sample, defining an n-dimensional matrix, where n is an integer 2 or higher, the matrix comprising a multiplicity of elements, each individual element identified by a unique matrix notation, the matrix notation comprising at least a separate dimensional index for each dimension of the array;
   (f) taking a sample from each of the multiplicity of biological fluid donations; (g) mapping each sample to one of said multiplicity of elements of the matrix, each individual sample identified by its corresponding element's respective matrix notation;
   (h) taking at least n aliquots from each sample;
   (i) forming from the at least n aliquots of each sample one unique subpool for each group of elements having matrix notations with one common dimensional index, each of the subpools containing sample aliquots taken exclusively from samples mapped to elements in which one of the dimensional indices is fixed;
   (j) testing all of the subpools for viral indication using a high-sensitivity PCR test;
   (k) determining the fixed dimensional index of each subpool that returns a positive viral indication;
   (l) combining said fixed dimensional indices to identify a subset of matrix elements that contain a viral positive sample, thereby reducing the number of elements that may contain a viral positive sample;
   (m) providing an indication to a user as to the identities of the subset of matrix elements that may contain a viral positive sample; and
   (n) where positive indications are provided in more than one subpool in more than one dimensional index of the matrix then directly testing each of the potentially positive samples with a high-sensitivity PCR test to detect the presence of the viral contamination, and producing a positive indication when the sample containing the presence of the viral contamination is detected.

2. The method according to claim 1 wherein n is 3, and the matrix is subdivided into rows, columns, and layers, wherein each element is characterized by a matrix notation $X_{rcs}$, where the dimensional indices r, c, and s, respectively, identify elements comprising a row, a column, and a layer of the matrix.

3. The method according to claim 2, wherein the subpool formation step (f) further comprises:
   forming r-subpools of aliquots from samples identified by a fixed r index but different c and s indices;
   forming c-subpools of aliquots from samples identified by a fixed c index but different r and s indices;
   forming s-subpools of aliquots from samples identified by a fixed s index but different r and c indices.

4. The method according to claim 3, further comprising the steps of:
   determining the fixed r index of each r-subpool which returned a positive viral indication;
   determining the fixed c index of each c which returned a positive viral indication; and
   determining the fixed s index of each s-subpool which returned a positive viral indication.

5. The method according to claim 4, further comprising the step of substituting the fixed r, c, and index of each r-, c-, and s-subpool which returned a positive viral indication for the dimensional indices r, c, and s of the matrix notation, thereby identifying a unique matrix element defined by said matrix notation, thus identifying the corresponding viral positive sample.

6. The method according to claim 1 wherein n is 2, and the matrix is subdivided into rows, and columns, wherein each element is characterized by a matrix notation $X_{rc}$ where the dimensional indices r, and c, respectively, identify elements comprising a row and a column of the matrix.

7. The method according to claim 6, wherein the subpool formation step (f) further comprises:
   forming r-subpools of aliquots from samples identified by a fixed r index but different c indices;
   forming c-subpools of aliquots from samples identified by a fixed c index but different r indices.

8. The method according to claim 7, further comprising the steps of:
   determining the fixed r index of each r-subpool which returned a positive viral indication; and
   determining the fixed c index of each c-subpool which returned a positive viral indication.

9. The method according to claim 8, further comprising the step of substituting the fixed r and c index of each r- and c-subpool which returned a positive viral indication for the dimensional indices r and c of the matrix notation, thereby identifying a unique matrix element defined by said matrix notation, thus identifying the corresponding viral positive sample.

10. The method according to claim 1, wherein said samples are collected concurrently with the collection of said multiplicity of biological fluid donations.

11. The method according to claim 2, wherein said samples are collected concurrently with the collection of said multiplicity of biological fluid donations.

12. The method according to claim 3, wherein said samples are collected concurrently with the collection of said multiplicity of biological fluid donations.

13. The method according to claim 4, wherein said samples are collected concurrently with the collection of said multiplicity of biological fluid donations.

14. The method according to claim 5, wherein said samples are collected concurrently with the collection of said multiplicity of biological fluid donations.

15. The method according to claim 6, wherein said samples are collected concurrently with the collection of said multiplicity of biological fluid donations.

16. The method according to claim 7, wherein said samples are collected concurrently with the collection of said multiplicity of biological fluid donations.

17. The method according to claim 8, wherein said samples are collected concurrently with the collection of said multiplicity of biological fluid donations.

18. The method according to claim 9, wherein said samples are collected concurrently with the collection of said multiplicity of biological fluid donations.

19. The method according to claim 1, wherein said samples are collected after the collection of said multiplicity of biological fluid donations.

20. The method according to claim 2, wherein said samples are collected after the collection of said multiplicity of biological fluid donations.

21. The method according to claim 3, wherein said samples are collected after the collection of said multiplicity of biological fluid donations.

22. The method according to claim 4, wherein said samples are collected after the collection of said multiplicity of biological fluid donations.

23. The method according to claim 5, wherein said samples are collected after the collection of said multiplicity of biological fluid donations.

24. The method according to claim 6, wherein said samples are collected after the collection of said multiplicity of biological fluid donations.

25. The method according to claim 7, wherein said samples are collected after the collection of said multiplicity of biological fluid donations.

26. The method according to claim 8, wherein said samples are collected after the collection of said multiplicity of biological fluid donations.

27. The method according to claim 9, wherein said samples are collected after the collection of said multiplicity of biological fluid donations.

28. The method according to claim 1, wherein said multiplicity of donations is more than 500 donations.

29. The method according to claim 2, wherein said multiplicity of donations is more than 500 donations.

30. The method according to claim 3, wherein said multiplicity of donations is more than 500 donations.

31. The method according to claim 4, wherein said multiplicity of donations is more than 500 donations.

32. The method according to claim 5, wherein said multiplicity of donations is more than 500 donations.

33. The method according to claim 6, wherein said multiplicity of donations is more than 500 donations.

34. The method according to claim 7, wherein said multiplicity of donations is more than 500 donations.

35. The method according to claim 8, wherein said multiplicity of donations is more than 500 donations.

36. The method according to claim 9, wherein said multiplicity of donations is more than 500 donations.

37. The method according to claim 1, wherein the biological fluid is blood.

38. The method according to claim 2, wherein the biological fluid is blood.

39. The method according to claim 3, wherein the biological fluid is blood.

40. The method according to claim 4, wherein the biological fluid is blood.

41. The method according to claim 5, wherein the biological fluid is blood.

42. The method according to claim 6, wherein the biological fluid is blood.

43. The method according to claim 7, wherein the biological fluid is blood.

44. The method according to claim 8, wherein the biological fluid is blood.

45. The method according to claim 9, wherein the biological fluid is blood.

46. The method according to claim 1, wherein the biological fluid is plasma.

47. The method according to claim 2, wherein the biological fluid is plasma.

48. The method according to claim 3, wherein the biological fluid is plasma.

49. The method according to claim 4, wherein the biological fluid is plasma.

50. The method according to claim 5, wherein the biological fluid is plasma.

51. The method according to claim 6, wherein the biological fluid is plasma.

52. The method according to claim 7, wherein the biological fluid is plasma.

53. The method according to claim 8, wherein the biological fluid is plasma.

54. The method according to claim 9, wherein the biological fluid is plasma.

55. The method according to claim 1, wherein the viral indication is an indication of a virus selected from the group consisting of HIV and HCV.

56. The method according to claim 2, wherein the viral indication is an indication of a virus selected from the group consisting of HIV and HCV.

57. The method according to claim 3, wherein the viral indication is an indication of a virus selected from the group consisting of HIV and HCV.

58. The method according to claim 4, wherein the viral indication is an indication of a virus selected from the group consisting of HIV and HCV.

59. The method according to claim 5, wherein the viral indication is an indication of a virus selected from the group consisting of HIV and HCV.

60. The method according to claim 6, wherein the viral indication is an indication of a virus selected from the group consisting of HIV and HCV.

61. The method according to claim 7, wherein the viral indication is an indication of a virus selected from the group consisting of HIV and HCV.

62. The method according to claim 8, wherein the viral indication is an indication of a virus selected from the group consisting of HIV and HCV.

63. The method according to claim 9, wherein the viral indication is an indication of a virus selected from the group consisting of HIV and HCV.

64. The method according claim 2, wherein the high-sensitivity test is PCR.

65. The method according claim 3, wherein the high-sensitivity test is PCR.

66. The method according claim 4, wherein the high-sensitivity test is PCR.

67. The method according claim 5, wherein the high-sensitivity test is PCR.

68. The method according to claim 1, wherein, the subset of matrix elements identifies at least one sample as a viral positive sample.

69. The method according to claim 2, wherein, the subset of matrix elements identifies at least one sample as a viral positive sample.

70. The method according to claim 3, wherein, the subset of matrix elements identifies at least one sample as a viral positive sample.

71. The method according to claim 4, wherein, the subset of matrix elements identifies at least one sample as a viral positive sample.

72. The method according to claim 5, wherein, the subset of matrix elements identifies at least one sample as a viral positive sample.

73. The method according to claim 6, wherein, the subset of matrix elements identifies at least one sample as a viral positive sample.

74. The method according to claim 7, wherein, the subset of matrix elements identifies at least one sample as a viral positive sample.

75. The method according to claim 8, wherein, the subset of matrix elements identifies at least one sample as a viral positive sample.

76. The method according to claim 9, wherein, the subset of matrix elements identifies at least one sample as a viral positive sample.

77. The method according to claim 1, wherein, the subset of matrix elements identifies a single sample as a viral positive sample.

78. The method according to claim 2, wherein, the subset of matrix elements identifies a single sample as a viral positive sample.

79. The method according to claim 3, wherein, the subset of matrix elements identifies a single sample as a viral positive sample.

80. The method according to claim 4, wherein, the subset of matrix elements identifies a single sample as a viral positive sample.

81. The method according to claim 5, wherein, the subset of matrix elements identifies a single sample as a viral positive sample.

82. The method according to claim 6, wherein, the subset of matrix elements identifies a single sample as a viral positive sample.

83. The method according to claim 7, wherein, the subset of matrix elements identifies a single sample as a viral positive sample.

84. The method according to claim 8, wherein, the subset of matrix elements identifies a single sample as a viral positive sample.

85. The method according to claim 9, wherein, the subset of matrix elements identifies a single sample as a viral positive sample.

86. The method according to claim 1, wherein, the number of indices in at least one dimension of the array is not equal to the number of indices in the other dimensions of the array.

87. The method according to claim 2, wherein, the number of indices in at least one dimension of the array is not equal to the number of indices in the other dimensions of the array.

88. The method according to claim 3, wherein, the number of indices in at least one dimension of the array is not equal to the number of indices in the other dimensions of the array.

89. The method according to claim 4, wherein, the number of indices in at least one dimension of the array is not equal to the number of indices in the other dimensions of the array.

90. The method according to claim 5, wherein, the number of indices in at least one dimension of the array is not equal to the number of indices in the other dimensions of the array.

91. The method according to claim 6, wherein, the number of indices in at least one dimension of the array is not equal to the number of indices in the other dimensions of the array.

92. The method according to claim 7, wherein, the number of indices in at least one dimension of the array is not equal to the number of indices in the other dimensions of the array.

93. The method according to claim 8, wherein, the number of indices in at least one dimension of the array is not equal to the number of indices in the other dimensions of the array.

94. The method according to claim 9, wherein, the number of indices in at least one dimension of the array is not equal to the number of indices in the other dimensions of the array.

* * * * *